United States Patent
Espina et al.

(10) Patent No.: US 9,096,833 B2
(45) Date of Patent: Aug. 4, 2015

(54) METHODS OF TREATING PRE-MALIGNANT DUCTAL CANCER WITH AUTOPHAGY INHIBITORS

(75) Inventors: Virginia Espina, Rockville, MD (US); Lance Liotta, Bethesda, MD (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 817 days.

(21) Appl. No.: 12/914,830

(22) Filed: Oct. 28, 2010

(65) Prior Publication Data

US 2011/0104065 A1    May 5, 2011

Related U.S. Application Data

(60) Provisional application No. 61/256,063, filed on Oct. 29, 2009.

(51) Int. Cl.
| | |
|---|---|
| *A61K 31/22* | (2006.01) |
| *A61K 31/4706* | (2006.01) |
| *A61K 31/52* | (2006.01) |
| *A61K 31/55* | (2006.01) |
| *A61K 31/704* | (2006.01) |
| *C12N 5/09* | (2010.01) |
| *G01N 33/53* | (2006.01) |
| *C12N 5/095* | (2010.01) |
| *A61K 45/06* | (2006.01) |
| *C12Q 1/68* | (2006.01) |
| *G01N 33/50* | (2006.01) |
| *G01N 33/574* | (2006.01) |

(52) U.S. Cl.
CPC ............... *C12N 5/0695* (2013.01); *A61K 31/22* (2013.01); *A61K 31/4706* (2013.01); *A61K 31/52* (2013.01); *A61K 31/55* (2013.01); *A61K 31/704* (2013.01); *A61K 45/06* (2013.01); *C12Q 1/6886* (2013.01); *G01N 33/5026* (2013.01); *G01N 33/57415* (2013.01); *C12Q 2600/118* (2013.01); *C12Q 2600/136* (2013.01)

(58) Field of Classification Search
None
See application file for complete search history.

(56) References Cited

FOREIGN PATENT DOCUMENTS

WO    WO2010/117715    * 10/2010

OTHER PUBLICATIONS

Damiani et al (Virchows Archive, 1999, vol. 434, pp. 227-234).*
Clinical Trials.Gov (Identifier NCT01023477, Dec. 1, 2009).*
Farnie et al (Journal of the National Cancer Institute, 2007, vol. 99, pp. 616-627).*
Park et al (Journal of Clinical Investigation, Feb. 2010, vol. 120, pp. 636-644).*
Espina et al (PLOS One, Apr. 2010, vol. 5, Issue 4, "Malignant Precursor Cells Pre-Exist in Human Breast DCIS and Require Autophagy for Survival").*
Chan et al (Cancer Research, 2002, vol. 62, pp. 122-128).*
Freshney, The Culture of Animal Cells, 1994, pp. 94-97.*

* cited by examiner

*Primary Examiner* — Karen Canella
(74) *Attorney, Agent, or Firm* — Foley & Lardner LLP

(57) ABSTRACT

Described herein are progenitor cancer cells and cell lines isolated from human breast ductal carcinoma in situ (DCIS) lesions and the uses of these cells or cell lines in drug design, drug screening, and monitoring in vivo therapy. The DCIS malignant precursor cells or cell lines are epithelial in origin, are positive for markers of autophagy, show at least one genetic difference from normal cells of said fragment, form 3-D tube-like structures or ball aggregates, or are inhibited in formation of 3-D structures and migration by treatment with chloroquine. In one embodiment, there is a loss of heterozygosity (LOH) that is narrowly confined to a region of chromosome 6p (6p21.1-6p12.3) that contains the SUPT3H gene.

19 Claims, 19 Drawing Sheets

Fig. 7 Cont.

METHODS OF TREATING PRE-MALIGNANT DUCTAL CANCER WITH AUTOPHAGY INHIBITORS

CROSS-REFERENCE TO RELATED PATENT APPLICATIONS

This application claims the benefit of U.S. Provisional Application No. 61/256,063, filed Oct. 29, 2009, which application is incorporated by reference in its entirety.

FEDERAL FUNDING STATEMENT

This invention was made with government support under Grant Number W81XWH-07-1-0377 awarded by the US Army, Department of Defense. The government has certain rights in the invention.

INTRODUCTION

Ductal Carcinoma In Situ (DCIS) is the most common type of malignant precursor of breast neoplasia in women [1-4]. DCIS accounts for an estimated 30% of the 185,000 breast cancers detected by mammography each year. While the majority, if not all, invasive breast carcinoma emerges from a premalignant stage, only one in five DCIS lesions recurs as metastatic carcinoma [5, 6]. New therapies are needed for the improved treatment of premalignant breast lesions such as DCIS. If the new therapy is relatively non-toxic, then the therapy could be applied within a neoadjuvant regimen or a chemoprevention regimen.

Despite this clinical need, two serious challenges exist: a) very little is known about the molecular origin of DCIS and the transition from in situ to invasive breast cancer, and b) it is impossible to rapidly assess the therapeutic efficacy of strategies for arresting breast cancer at the pre-invasive stage. Since premalignant breast lesions can persist for five years or more before the transition to invasive carcinoma, evaluation of a candidate therapy will require a waiting time of at least five years before the therapeutic efficacy is known. The present invention addresses both of these therapeutic challenges and offers a novel therapeutic target for premalignant breast lesions.

SUMMARY

In one aspect, there is provided an isolated population of human breast ductal carcinoma in situ (DCIS) cells obtained from a fragment of breast tissue, wherein the cells (i) are epithelial in origin, (ii) comprise one or more markers of autophagy, (iii) show at least one genetic difference from normal cells, (iv) form 3-D spheroids or duct-like structures or ball aggregates and (v) are inhibited in formation of 3-D structures and migration by treatment with chloroquine. In one embodiment, the cells express an increased level of one or more of CD44, COX2 or MMP-14, or a decreased level of CD24 or E-Cadherin compared to monolayer anchorage dependent epithelial cells. In another, the genetic difference is selected from the group consisting of a loss of copy number of 6p21.1 to 6p12.3, a loss of heterozygosity at SUPT3H gene, a gain of copy number at 5p12 to 5p13.3 or a gain of copy number at 17q22 to 17q25.1. In one embodiment, the population comprises the cells of the cell line deposited at ATCC on Mar. 18, 2010 and accorded ATCC No. PTA-10730.

In another aspect, methods are provided for making a strain of human breast ductal carcinoma in situ (DCIS) cells from a patient comprising (A) establishing in a container a serum-free organ culture comprising fragments of breast tissue containing stroma, adipose and ductal elements, among which are ductal carcinoma in situ lesions, and (B) allowing the tissue to attach to the container and allowing the DCIS cells to migrate out of the tissue such that the DCIS cells without enzymatic dissociation or immortalization spontaneously form 3-D spherical and ductal tubular structures that contain cells that show at least one genetic difference from normal cells.

In addition, methods are provided for assessing whether a potential therapeutic agent is useful for the treatment of pre-neoplastic lesions of the breast comprising administering in vitro the potential therapeutic agent to the population of DCIS cells as described herein, culturing the cells, and determining whether the therapeutic agent inhibits the growth of the cells, proliferation of the cells or tendency of the cells to invade or metastasize. In one, embodiment, the determination step involves evaluating exposed DCIS cells for autophagy, while in another, the determination step involves histomorphologically evaluating exposed DCIS cells.

In another aspect, methods of assessing whether a potential therapeutic agent is useful for the treatment of pre-neoplastic lesions of the breast comprise transplanting a population of DCIS cells of claim 1 to a non-human animal model, administering the potential therapeutic agent to the xenotransplant, and determining whether the therapeutic agent inhibits the growth of the cells, proliferation of the cells or tendency of the cells to invade or metastasize.

In another, methods of selecting a treatment for a patient with pre-neoplastic lesions of the breast comprise (A) isolating from the patient human breast ductal carcinoma in situ (DCIS) cells as described herein; (B) administering in vitro a potential therapeutic agent to the DCIS cells; (C) culturing the cells; and (D) determining whether the therapeutic agent inhibits the growth of the cells, proliferation of the cells or tendency of the cells to invade or metastasize; and (E) selecting a treatment based upon the determination. In some embodiments, steps (A) to (D) can be repeated after a selected treatment has been administered to the patient.

In one aspect, methods of monitoring the efficacy of a treatment of a patient with preneoplastic lesions of the breast, comprise (A) isolating from the patient human breast ductal carcinoma in situ (DCIS) cells as described herein; (B) administering in vitro the potential therapeutic agent to the DCIS cells; (C) culturing the cells; and (D) determining whether the therapeutic agent inhibits the growth of the cells, proliferation of the cells or tendency of the cells to invade or metastasize. In some embodiments, steps (A) to (D) are performed more than once during the course of treatment.

In another aspect, methods for preventing or limiting progression of a pre-malignant breast lesion in a patient comprise identifying in the patient a pre-malignant breast lesion and administering to the patient an effective amount of an autophagy inhibitor selected from the group consisting of chloroquine, hydroxychloroquine, 3-methyladenie, clomipramine, ethyl pyruvate and glycyrrhizin. In one embodiment, the autophagy inhibitor is chloroquine. In another, the identification step involves evaluating the lesion for the presence of a DCIS malignant precursor cell (DMPC). In another, the autophagy inhibitor is administered in combination with a chemotherapeutic agent, such as a kinase inhibitor. In some aspects, the kinase inhibitor can be an estrogen modulator, such as tamoxifen, or an aromatase inhibitor.

Similarly, methods for treating a pre-malignant breast lesion in a patient comprise identifying in the patient a pre-malignant breast lesion and administering to the patient an effective amount of an autophagy inhibitor selected from the group consisting of chloroquine, hydroxychloroquine, 3-methyladenie, clomipramine, ethyl pyruvate and glycyrrhizin. In one embodiment, the autophagy inhibitor is chloroquine. In another, the identification step involves evaluating the lesion for the presence of a DCIS malignant precursor cell (DMPC). In another, the autophagy inhibitor is administered in combination with a chemotherapeutic agent, such as a kinase inhibitor. In some aspects, the kinase inhibitor can be an estrogen modulator, such as tamoxifen, or an aromatase inhibitor.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the prior art.

DETAILED DESCRIPTION

Figure 1:
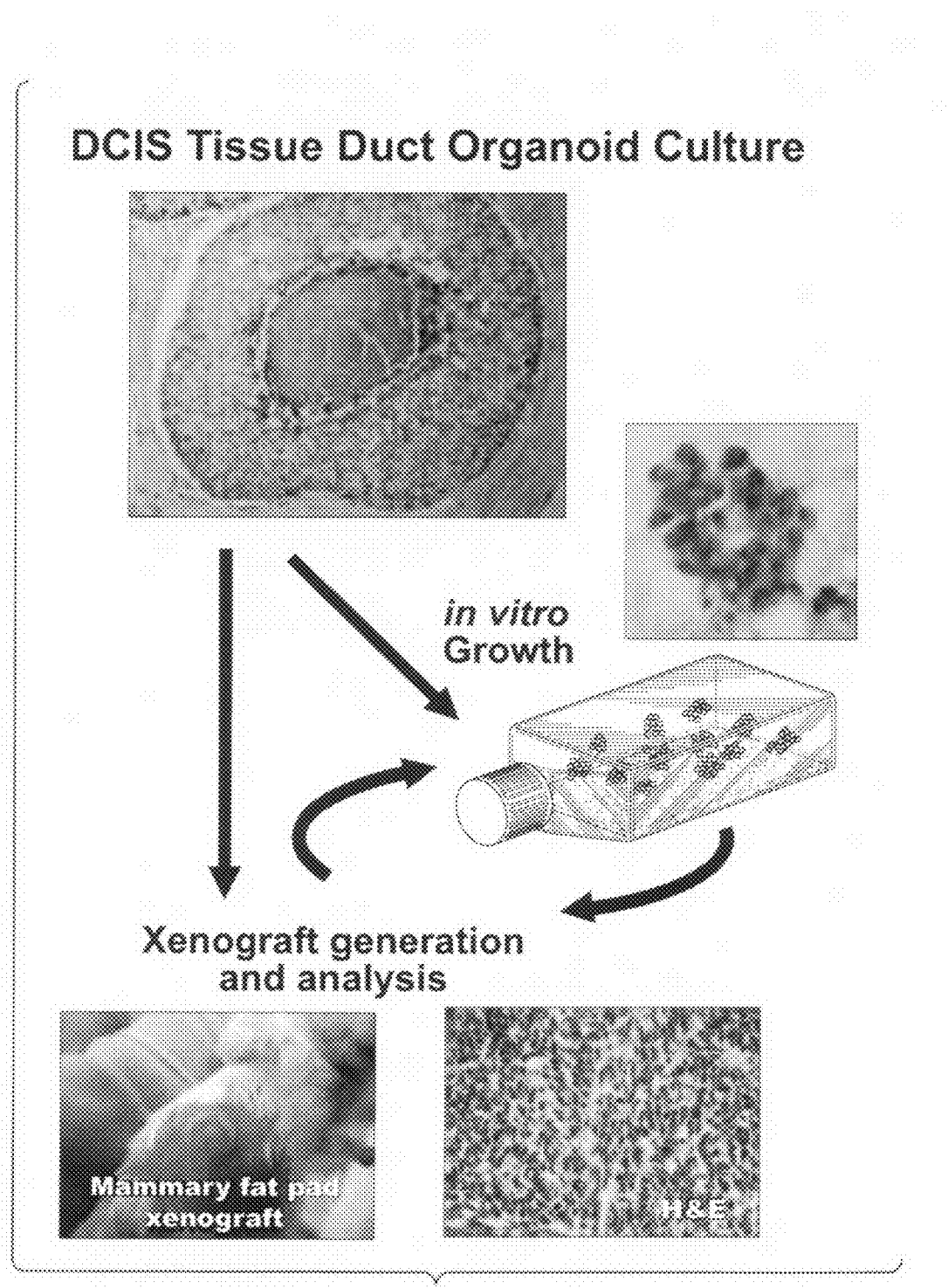
FIG. 1 illustrates a tissue culture procedure for growing DCIS organoids that yield epithelial outgrowths for in vitro and in vivo models.
Figure 2A:
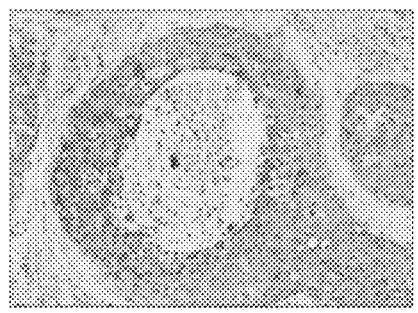
FIG. 2A-F shows that human DCIS tissue generates spheroids and pseudoductal structures in ex vivo culture and xenograft neoplasms. (A) H&E stain of human breast DCIS, grade III with comedo necrosis (case 08-352), that represents the primary surgical source material for the organoid culture model system. (B) Human pure DCIS organoids or spheroids transplanted in NOD SCID mice induced tumor formation (arrow) at the mammary fat pad transplantation site within 2 months. (C) H&E stain of murine xenograft tumor (mouse 792, 100×). Note pleomorphic epithelial cells with prominent nucleoli, stromal invasion and partial glandular differentiation. Organoid culture of human DCIS lesions in serum free conditions spontaneously yielded (D) epithelial spheroids (10× magnification) with a single spheroid shown in (E) (40×) and (F) pseudoductal structures with lumen formation (arrow) (40×).
Figure 2B:
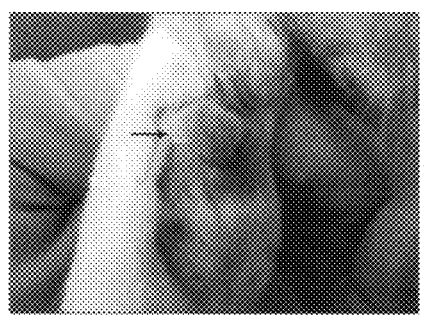
Figure 2C:
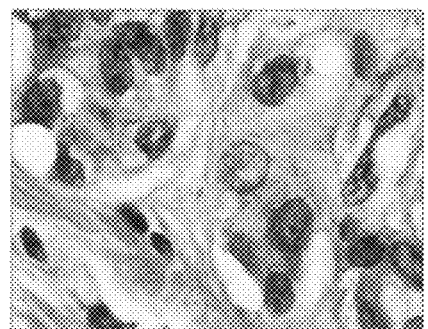
Figure 2D:
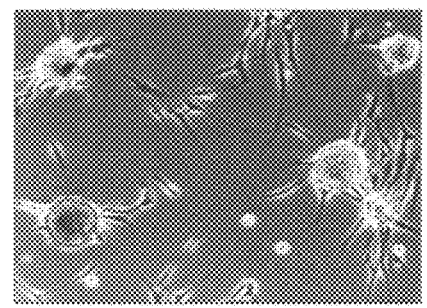
Figure 2E:
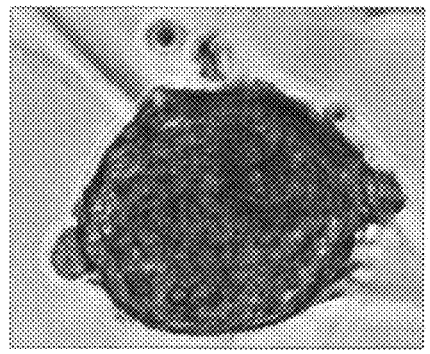
Figure 2F:
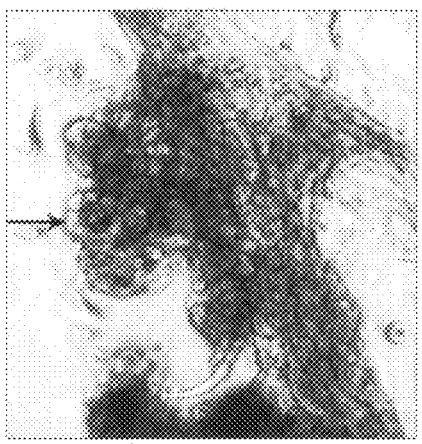
Figure 3A:
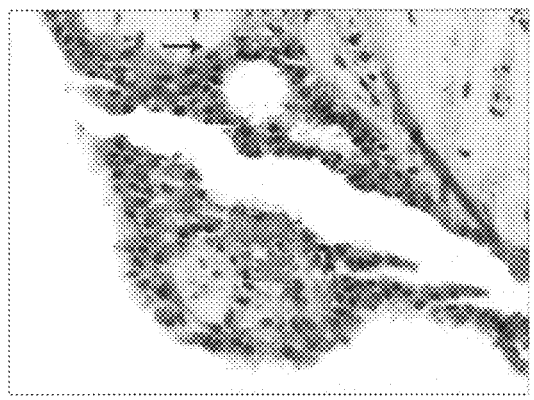
FIG. 3A-D show multi-layered growth and invasion of DCIS cultured epithelial cells on autologous breast stroma. DCIS epithelial cells grown from human tissue explants in organoid culture were shown to have neoplastic characteristics as shown by their ability to migrate over the surface of autologous breast stroma, form multi-layered colonies, and invade inward into the stroma. (A) H&E stain of formalin fixed DCIS organoid after 12 weeks in culture. A multi-layered DCIS colony has invaded autologous breast stroma (20×). (B) H&E stain of multi-layered pleomorphic epithelial cells (arrow) on surface of autologous breast stroma after 12 weeks in culture (20×). (C) DCIS cultured neoplastic cell autologous stromal invasion (20×). (D) Example of DCIS multilayered colony on autologous breast stroma in culture for 5 weeks (10×). Cytogenetic analysis of all example cases shown revealed chromosome 6p copy number loss (FIG. 8).
Figure 3B:
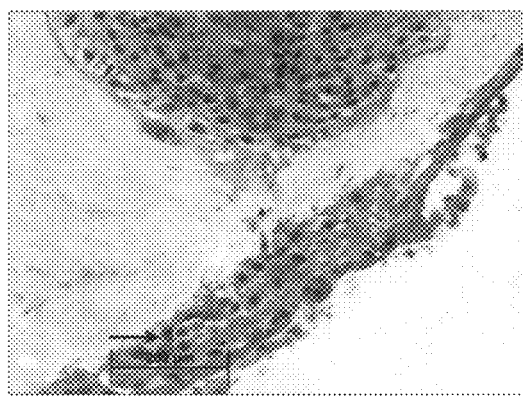
Figure 3C:
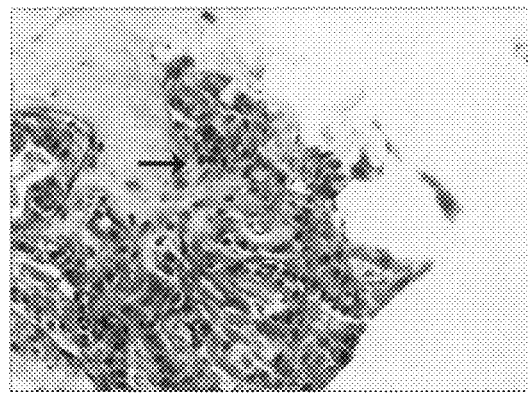
Figure 3D:
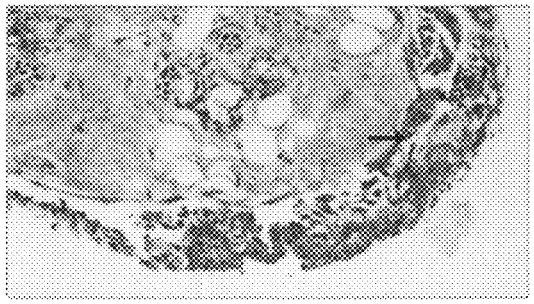

Progenitor cancer cells have been discovered in human breast ductal carcinoma in situ (DCIS) lesions. The DCIS malignant precursor cells (DMPC) were isolated from the fresh living human DCIS lesions and propagated into cell strains. These cells are characterized by a) invasive growth b) formation of 3-Dimensional spherical or tubular structures without enzymatic treatment or requirement for a collagen gel growth medium, and c) cytogenetic abnormalities distinct from the normal cells of the patient donor. The cells are useful in drug design and drug screening. In addition, isolated DMPC from a patient can be used to evaluate and monitor the efficacy of potential therapies. The DCIS cells are shown to be dependent on cellular autophagy for survival, and inhibition of autophagy suppresses or destroys the DCIS cells. Thus, in another aspect, methods of treating, or limiting the progression of, pre-malignant breast lesions are provided.

DEFINITIONS

As used herein, the term "lesion" refers to any abnormal tissue found on or in an organism, usually damaged by disease or trauma. A lesion can be a cancer or precancerous tissue which can be isolated by surgical procedure, for example, biopsy.

As used herein, the term "preneoplastic" refers to a tumorigenesis stage preceding the formation of a benign or malignant neoplasm. "Neoplasm", as used herein, refers to an abnormal mass of tissue as a result of neoplasia. Neoplasia is the abnormal proliferation of cells. The growth of this clone of cells can exceed, and can be uncoordinated with, that of the normal tissues around it. It usually causes a lump or tumor. Neoplasms can be benign, pre-malignant or malignant.

The term "pre-neoplastic lesion", as used herein, refers to a lesion of pre-neoplastic stage.

A "population" of cells intends a collection of more than one cell that is identical (clonal) or non-identical in phenotype and/or genotype.

As used herein, the term "propagate" means to grow or cultivate a population of cells. The term "growing" refers to the proliferation of cells in the presence of supporting media, nutrients, growth factors, support cells, or any chemical or biological compound necessary for obtaining the desired number of cells or cell type. In one embodiment, the growing of cells results in the regeneration of tissue.

As used herein, the term "culturing" refers to the in vitro propagation of cells or organisms on or in media of various kinds. It is understood that the descendants of a cell grown in culture may not be completely identical (i.e., morphologically, genetically, or phenotypically) to the parent cell. By "expanded" is meant any proliferation or division of cells.

As used herein, the "lineage" of a cell defines the heredity of the cell, i.e. its predecessors and progeny. The lineage of a cell places the cell within a hereditary scheme of development and differentiation.

As used herein, the term "CD44" refers to a protein having an amino acid sequence substantially identical to, or a mammalian protein homologue or isoform of, the human CD44 sequence of GenBank Accession No. NP_000601. Suitable cDNA encoding CD44 is provided at GenBank Accession No. NM_00061. "CD44" is a cell-surface glycoprotein involved in cell-cell interactions, cell adhesion and migration. It is a receptor for hyaluronic acid (HA) and can also interact with other ligands, such as osteopontin, collagens, and matrix metalloproteinases (MMPs). This protein participates in a wide variety of cellular functions including lymphocyte activation, recirculation and homing, hematopoiesis, and tumor metastasis. CD44 has been reported as cell a surface marker for breast and prostate cancer stem cells.

As used herein, the term "COX2", "Prostaglandin-endoperoxide synthase (PTGS)" or "cyclooxygenase" refers to a protein having an amino acid sequence substantially identical to, or a mammalian protein homologue or isoform of, the human COX2 sequence of GenBank Accession No. NP_000954. Suitable cDNA encoding COX2 is provided at GenBank Accession No. NM_000963. "COX2" is a key enzyme in prostaglandin biosynthesis, which acts both as a dioxygenase and as a peroxidase. COX2 is regulated by specific stimulatory events, suggesting that it is responsible for the prostanoid biosynthesis involved in inflammation and mitogenesis.

As used herein, the term "MMP-14", or "matrix metallopeptidase 14" refers to a protein having an amino acid sequence substantially identical to, or a mammalian protein homologue or isoform of, the human MMP-14 sequence of GenBank Accession No. NP_004986. Suitable cDNA encoding MMP-14 is provided at GenBank Accession No. NM_004995. MMP-14 a protein of the matrix metalloproteinase (MMP) family that is involved in the breakdown of extracellular matrix in normal physiological processes, such as embryonic development, reproduction, and tissue remodeling, as well as in disease processes, such as arthritis and metastasis. Most MMP's are secreted as inactive proproteins which are activated when cleaved by extracellular proteinases. However, the protein encoded by this gene is a member of the membrane-type MMP (MT-MMP) subfamily; each member of this subfamily contains a potential transmembrane domain suggesting that these proteins are expressed at the cell surface rather than secreted. This protein activates MMP2 protein, and this activity may be involved in tumor invasion. Representative GenBank Accession Numbers for MMP-14 include NP_004986 for protein and NM_004995 for nucleotide sequences.

As used herein, the term "CD24" refers to a protein having an amino acid sequence substantially identical to, or a mammalian protein homologue or isoform of, the human CD24 sequence of GenBank Accession No. NP_037362. Suitable cDNA encoding CD24 is provided at GenBank Accession No. NM_013230.

As used herein, the term "E-cadherin" refers to a protein having an amino acid sequence substantially identical to, or a mammalian protein homologue or isoform of, the human E-cadherin sequence of GenBank Accession No. NP_004351. Suitable cDNA encoding E-cadherin is provided at GenBank Accession No. NM_004360. E-cadherin is from the cadherin superfamily. The encoded protein is a calcium dependent cell-cell adhesion glycoprotein comprised of five extracellular cadherin repeats, a transmembrane region and a highly conserved cytoplasmic tail. Mutations in this gene are correlated with gastric, breast, colorectal, thyroid and ovarian cancer. Loss of function is thought to contribute to progression in cancer by increasing proliferation, invasion, and/or metastasis.

As used herein, the term "SUPT3H", "transcription initiation protein SPT3 homolog" or "suppressor of Ty 3 homolog" refers to a protein having an amino acid sequence substantially identical to, or a mammalian protein homologue or isoform of, the human SUPT3H sequence of GenBank Accession No. NP_003590. Suitable cDNA encoding SUPT3H is provided at GenBank Accession No. NM_003599. In one embodiment, the present disclosure provides a loss of heterozygosity (LOH) that is narrowly confined to a region of chromosome 6p (6p21.1-6p12.3) that contains one gene, SUPT3H. This LOH is associated with the human breast ductal carcinoma in situ (DCIS) progenitor cell phenotype. Breast DCIS cells with this abnormal phenotype (i.e. exhibiting the LOH) are prevented from forming out growths (ex vivo) in the presence of Chloroquine (50 mM). Since this genetic alteration is a LOH it implies a suppressor function for the protein product of this gene. Consequently the protein product of this gene is a potential therapeutic target for preventing DCIS and/or invasive breast carcinoma. Restoring the missing function of this gene could be a therapy for preventing DCIS and/or invasive breast cancer. Thus, SUPT3H could be used as a new prognostic/diagnostic marker or method for selecting human breast DCIS cells with invasive potential. The treatment target is the autophagy pathway, and an exemplary treatment agent is chloroquine, which could be used for chemoprevention.

The term "autophagy" or "autophagocytosis", as used herein, refers to a catabolic process involving the degradation of a cell's own components through the lysosomal machinery. It is a tightly-regulated process that plays a normal part in cell growth, development, and homeostasis, helping to maintain a balance between the synthesis, degradation, and subsequent recycling of cellular products. It is a major mechanism by which a starving cell reallocates nutrients from unnecessary processes to more-essential processes. A variety of autophagic processes exist, all having in common the degradation of intracellular components via the lysosome. Markers, or "autophagy markers", are known in the art to identify the occurrence of the autophagy process in a cell. Non-limiting examples of autophagy markers include LC3B, Atg5, Beclin-1, mTOR, and phosphorylation of Akt on serine 473.

As used herein, the term "LC3B", "MAP1LC3B" or "microtubule-associated protein 1 light chain 3 beta" refers to a protein having an amino acid sequence substantially identical to, or a mammalian protein homologue or isoform of, the human LC3B sequence of GenBank Accession No. NP_073729. Suitable cDNA encoding LC3B is provided at GenBank Accession No. NM_022818. LC3B is a subunit of neuronal microtubule-associated MAP1A and MAP1B proteins, which are involved in microtubule assembly and important for neurogenesis. Research in rat has shown a role for this gene in autophagy, a process that involves the bulk degradation of cytoplasmic component.

As used herein, the term "Atg5", or "microtubule ATG5 autophagy related 5 homolog" refers to a protein having an amino acid sequence substantially identical to, or a mammalian protein homologue or isoform of, the human Atg5 sequence of GenBank Accession No. NP_004840. Suitable cDNA encoding Atg5 is provided at GenBank Accession No. NM_004849.

As used herein, the term "Beclin-1", "BECN1" or "beclin 1, autophagy related" refers to a protein having an amino acid sequence substantially identical to, or a mammalian protein homologue or isoform of, the human Beclin-1 sequence of GenBank Accession No. NP_003757. Suitable cDNA encoding Beclin-1 is provided at GenBank Accession No. NM_003766.

As used herein, the term "mTOR", or "mechanistic target of rapamycin" refers to a protein having an amino acid sequence substantially identical to, or a mammalian protein homologue or isoform of, the human Beclin-1 sequence of GenBank Accession No. NP_004949. Suitable cDNA encoding Beclin-1 is provided at GenBank Accession No. 1.NM_004958. The protein encoded by this gene belongs to a family of phosphatidylinositol kinase-related kinases. These kinases mediate cellular responses to stresses such as DNA damage and nutrient deprivation.

As used herein, the term "Akt", "Akt1" or "v-akt murine thymoma viral oncogene homolog" refers to a protein having an amino acid sequence substantially identical to, or a mammalian protein homologue or isoform of, the human LC3B sequence of GenBank Accession No. NP_001014431. Suitable cDNA encoding LC3B is provided at GenBank Accession No. NM_001014431. AKT is a mediator of growth factor-induced neuronal survival. Survival factors can suppress apoptosis in a transcription-independent manner by activating the serine/threonine kinase AKT, which then phosphorylates and inactivates components of the apoptotic machinery.

As used herein, the term "epithelial membrane antigen" or "EMA" refers to an antigen expressed on the surface of an epithelial cell. EMA belongs to a heterogeneous family of highly-glycosylated transmembrane proteins known as human milk fat globule (HMFG) membrane proteins. This family of antigens is not restricted to breast but may also be found in secretory epithelial cells, to a lesser degree, in non-secretory epithelium (e.g., squamous epithelium) and rarely in nonepithelial cells. A non-limiting example of EMA is Epithelial cell adhesion molecule (EpCAM), a protein that in humans is encoded by the EPCAM gene. A representative mRNA sequence is GeneBank Accession No. NM 002354, and protein sequence is GeneBank Accession No. NP_002345.

As used herein, the term "chloroquine" refers to N'-(7-chloroquinolin-4-yl)-N,N-diethyl-pentane-1,4-diamine. A "chemical equivalent of chloroquine", as used herein, refers to a 4-aminoquinoline that is structurally similar to chloroquine and/or has anti-malarial or anti-autophagy activity.

DCIS Malignant Precursor Cells

In one aspect, an isolated living human breast ductal carcinoma in situ (DCIS) malignant precursor cell is provided. In one embodiment, the DCIS malignant precursor cell is potentially malignant or invasive. In another embodiment, the DCIS malignant precursor cell is cytogenetically abnormal. In yet another embodiment, the DCIS malignant precursor cell requires cellular autophagy for survival.

In one embodiment the malignant or invasive potential of the DCIS malignant precursor cell can be identified by the cell's anchorage independent growth and migration or ability to form 3-D structures. Non-limiting examples of 3-D structures include spheroids, duct-like structures, tube-like structures, epithelial or cuboidal cobblestone sheets or differentiated structures.

The malignant or invasive potential of the DCIS malignant precursor cell can further or alternatively be identified by the cell's ability to be propagated without exogenous immortalization. In one aspect, the DCIS malignant precursor cell can be propagated for at least about a month, or alternatively at least about two, about three, about six, about 12 or about 24 months. In another aspect, the DCIS malignant precursor cell can be propagated for at least about 10 passages, or alternatively for at least about 20 passages, about 30 passages, about 50 passages or about 100 passages.

The malignant or invasive potential of the DCIS malignant precursor cell can further or alternatively be identified by the cell's ability to invade autologous stroma in organ culture.

The malignant or invasive potential of the DCIS malignant precursor cell can further or alternatively be identified by the cell's ability to generate tumors when transplanted into NOD SCID mice. In one aspect, the tumors can be observed at about a month after transplantation. In another aspect, the tumors can be observed at about two months after transplantation. In yet another aspect, the tumors can be observed at between one month and six months after transplantation.

In another embodiment, the DCIS malignant precursor cell is cytogenetically abnormal. Non-limiting examples of cytogenetic abnormality include loss or gain of chromosome copy numbers, such as loss of copy number on chromosome 5, 6, 8 or 13 or gain of copy number on chromosome 1, 5 and 17. In one aspect, the cytogenetic abnormality is loss of chromosome or loss of heterozygosity of chromosome 6 (p21.1/p12.3). In another aspect, the cytogenetic abnormality is loss of heterozygosity of the SUPT3H gene. In yet another aspect, the cytogenetic abnormality is gain of copy number of 5p12 to 5p13.3. In another aspect, the cytogenetic abnormality is gain of copy number of 17q22 to 17q25.1.

In yet another embodiment, the DCIS malignant precursor cell requires cellular autophagy for survival. In one aspect, therefore, the DCIS malignant precursor cell can be identified by one or more autophagy markers. Non-limiting examples of autophagy markers include LC3B, Atg5, Beclin-1, mTOR, and phosphorylation of Akt on serine 473. Accordingly, an increased expression of LC3B, Atg5, Beclin-1 or mTOR in the DCIS cell, or an increased phosphorylation of Akt on serine 473 identifies the DCIS cell as a DCIS malignant precursor cell. The increase of expression or phosphorylation of the autophagy markers, in some embodiments, can be at least about 10%, about 20%, about 30%, about 50%, about 100%, about 150%, about 2 folds, about 3 folds, about 5 folds, about 10 folds, or about 20 folds of the expression of the corresponding marker in a suitable control sample. A suitable control sample can be a normal breast stroma cell or tissue.

In another aspect, the DCIS malignant precursor cell can further or alternatively be identified by the inhibition of its growth, migration or invasion by an autophagy inhibitor.

Non-limiting examples of autophagy inhibitors include chloroquine, 4-aminoquinoline or a chemical equivalent thereof. In a particular aspect, the formation of 3-D structures by the DCIS malignant precursor cells can be inhibited by contacting the cell with chloroquine, a 4-aminoquinoline or a chemical equivalent thereof.

In some embodiments, the provided DCIS malignant precursor cell has high or increased expression of CD44, COX2 and MMP-14, or low or decreased expression of CD24 or E-Cadherin, as compared to a suitable control sample, such as a duct epithelial cell that is not neoplastic. The increase of expression of the cell surface markers, in some embodiments, can be at least about 10%, about 20%, about 30%, about 50%, about 100%, about 150%, about 2 folds, about 3 folds, about 5 folds, about 10 folds, or about 20 folds of the expression of the corresponding marker in the suitable control sample. The decrease of expression of the cell surface markers, in some embodiments, can be at least about 5%, about 10%, about 20%, about 30%, about 40%, about 50%, about 60%, about 70%, about 80%, about 90% or about 95% of the expression of the corresponding marker in the suitable control sample.

In another aspect, DCIS malignant precursor cells can exhibit signal pathway activation of prosurvival, autophagy, cell migration, cell adhesion, hypoxia, genetic instability, proteosome, or stem cell related pathways.

In some embodiments, the DCIS malignant precursor cell is of epithelial origin. The epithelial origin of the DCIS malignant precursor cell can be tested with an epithelial membrane antigen (EMA) such as the epithelial cell adhesion molecule (EpCAM).

In one embodiment, an isolated population of human breast ductal carcinoma in situ (DCIS) cells obtained from a fragment of breast tissue is provided, wherein the cells (i) are epithelial in origin, (ii) are positive for markers of autophagy, (iii) show at least one genetic difference from normal cells, (iv) form 3-D spheroids or duct-like structures or ball aggregates and (v) are inhibited in formation of 3-D structures and migration by treatment with chloroquine, a 4-aminoquinoline or a chemical equivalent thereof.

Distinguishing Genetic Features

DCIS malignant precursor cells are cytogenetically abnormal compared to normal or non-neoplastic cells. The DCIS malignant precursor cells can display a loss of heterozygosity (LOH) in a narrowly confined region of chromosome 6p (6p21.1-6p12.3) that contains the gene SUPT3H (Transcription initiation protein SPT3 homolog). Thus, in one embodiment, the DCIS malignant precursor cells can be identified by a LOH in SUPT3H. Other non-limiting examples of cytogenetic abnormality include loss or gain of chromosome copy numbers, such as loss of copy number on chromosome 5, 6, 8 or 13 or gain of copy number on chromosome 1, 5 and 17. In one aspect, the cytogenetic abnormality is gain of copy number of 5p12 to 5p13.3. In another aspect, the cytogenetic abnormality is gain of copy number of 17q22 to 17q25.1.

In another aspect, the DCIS progenitor cells comprise the cells of the cell line deposited with the American Type Culture Collection, P.O. Box 1549, Manassas, Va., USA, 2010 on Mar. 18, 2010 and accorded ATCC Accession No. PTA-10730.

Methods of Making

In another aspect, a method for preparing an isolated malignant precursor human breast ductal carcinoma in situ (DCIS) cell or a strain of such cells from a patient comprises (A) establishing in a container a serum-free organ culture comprising fragments of breast tissue containing stroma, adipose and ductal elements, which include ductal carcinoma in situ (DCIS) lesions, and (B) allowing the tissue to attach to the container and the DCIS cells to migrate out of the tissue and spontaneously form 3-D spheroids and tubular structures in serum free media without enzymatic dissociation and migrate on the surface of autologous breast stroma (FIGS. 1-3). In one embodiment, the DCIS cells migrating on the autologous stroma invade the stroma. In another, the morphology of the DCIS ductal lesion in the fragment of human breast tissue is maintained for at least 6 weeks.

The breast lesions can be rinsed with a buffer, such as phosphate buffered saline (PBS), prior to culturing. The buffer may contain antibiotic and/or anti-fungal agents such as, but not limited to gentamicin and streptomycin. The lesions then can be minced into small pieces and suspended in dissociation media. The dissociation media can be basal media supplemented with a cell dissociation agent, such as but not limited to EDTA, EGTA, trypsin and collagenase-dispase.

The dissociated cells or cell aggregates then can be pelleted by centrifugation and resuspended in basal medium, and transferred to a culture dish.

In one embodiment, the breast lesions can be rinsed in a variety of basal media, prior to culturing. The basal medium may contain antibiotic and/or anti-fungal agents such as, but not limited to, gentamycin and streptomycin. The lesions then can be minced into small pieces and cultured directly in a culture dish without dissociation.

A wide variety of basal media can be used to keep the pH of the liquid in a range that promotes survival of DCIS malignant precursor cells. Non-limiting examples include F12/DMEM, Ham's F10 (Sigma), CMRL-1066, Minimal essential medium (MEM, Sigma), RPMI-1640 (Sigma), Dulbecco's Modified Eagle's Medium (DMEM, Sigma), OPTI-MEM® (GIBCO BRL) and Iscove's Modified Eagle's Medium (IMEM). In one embodiment, nutrients can be added to supplement the basal medium. In another, growth factors or hormones can be added to supplement the basal medium, such as, but not limited to, EGF, insulin and estrogen.

DCIS malignant precursor cells can migrate out of the cell aggregates into the medium and anchor to the culture dish or other supplied anchor material. The remnant of the minced tissues that do not attach to the culture dish or anchor will flow in the medium and will be removed by medium change.

In another embodiment, cells from the cell aggregates placed in media all attach to the culture dish and the DCIS malignant precursor cells can slowly establish and grow among the other cell types. Eventually, the DCIS malignant precursor cells will form a substantially pure population of cells and the other cell types will no longer be in the culture. The culture process and environment will not support the replication and/or survival of contaminating cell types and will promote the survival and growth of the human cancer stem cells so as to generate a substantially pure population of DCIS malignant precursor cells growing as 3-D structures such as spheroids (FIGS. 1-3).

Screening Methods

In another aspect, a method of assessing whether a potential therapeutic agent is useful for the treatment of pre-neoplastic lesions of the breast comprises administering in vitro the potential therapeutic agent to a population of the DCIS malignant precursor cells of any of the above embodiments, culturing the cells, and determining whether the therapeutic agent inhibits the growth of the cells, proliferation of the cells or tendency of the cells to invade or to metastasize. The determination step can involve assessment of reversal of the invasive or progenitor characteristics of the DCIS malignant precursor cells as described supra.

Figure 13A:
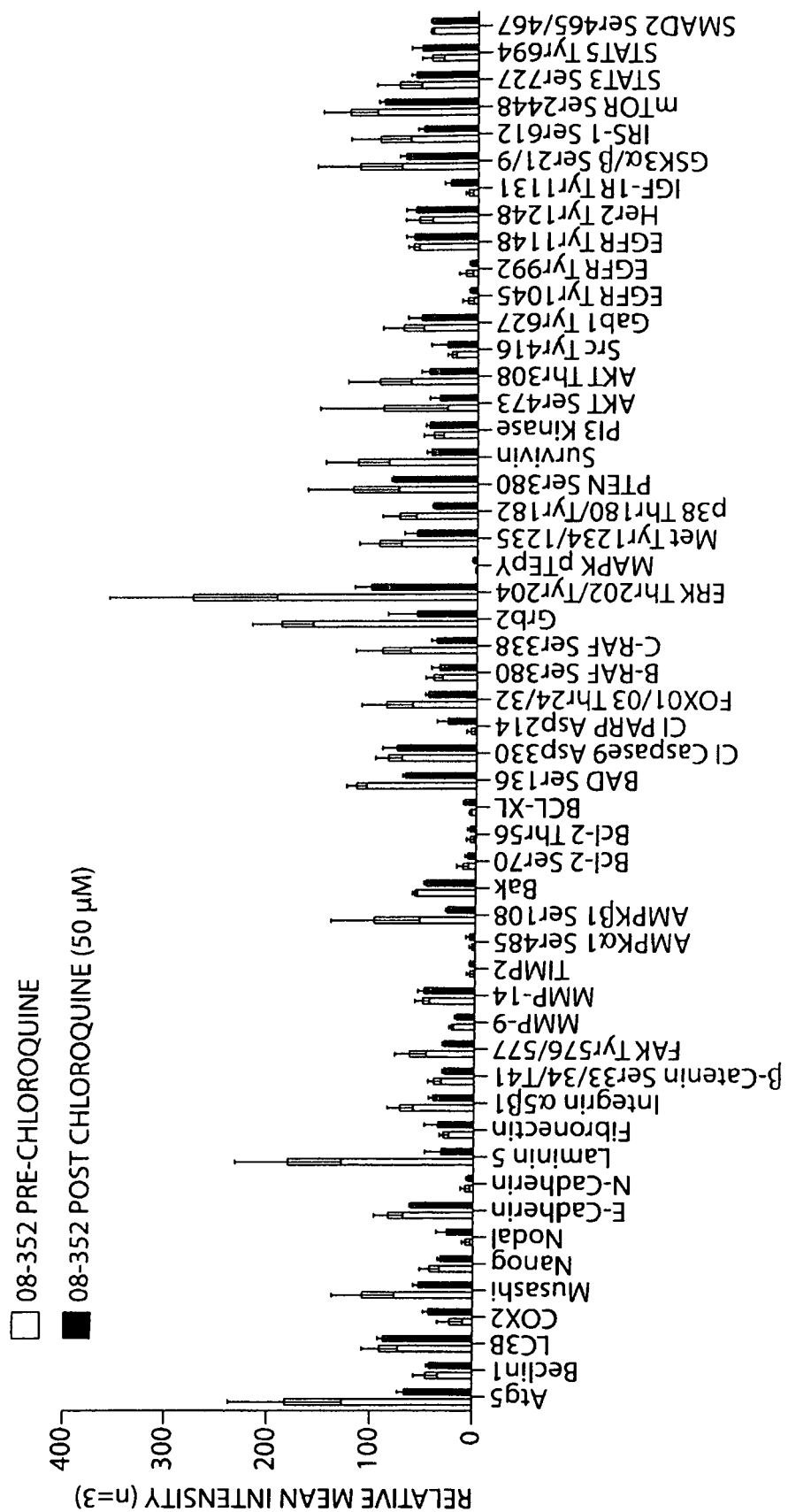
FIG. 13A-C show that chloroquine suppresses DCIS neoplastic cell outgrowth and spheroid formation and alters cellular signaling. Chloroquine inhibits autophagy by disrupting the autophagosomes/lysosome cascade. A DCIS culture was maintained in DMEM/F12 culture medium supplemented with EGF, insulin, gentamicin and streptomycin. After epithelial cells and spheroids formed in culture, the medium was treated with chloroquine phosphate (50 µM) for 4 days. Spheroids were harvested pre and post chloroquine treatment. (A) Chloroquine markedly inhibited autophagy associated pathways as shown by a reduction in autophagy pathway proteins (Atg5, AKT Ser473, AKT Thr308, APMKβ1 Ser108, ERK Thr202/Tyr204, mTOR Ser2448), adhesion proteins (Laminin5, Integrin α5β1), and proliferation/survival proteins (Musashi, Bad Ser136, c-RAF Ser338, GSK3α/β, Ser21/9, IRS-1 Ser612, Survivin, FOX01/03 Thr24/32, Grb2, c-RAF Ser338, Met Tyr1234/1235, p38 MAPK Thr1801Tyr182, PTEN Ser380) (n=3, ±SEM). (B) Chloroquine suppressed outgrowth of DCIS epithelial cells in culture as measured by the diameter of the outgrowth. Two axis diameters were measured for multiple organoids for two cases. The mean diameter of case 09-148-A outgrowth prior to treatment (open circle) was 0.85 cm±0.11 (n=15, mean±SEM) and after chloroquine treatment (black circle), the mean diameter was 0.084 cm±0.03 (n=23, mean±SEM) (p<0.0001). In the second series of organoid cultures, the mean diameter of case 09-148-B outgrowth prior to treatment (open triangle) was 1.36±0.25 (n=8, mean±SEM) while the chloroquine treated outgrowth (black triangle) mean diameter was 0.21±0.03 (n=7, mean±SEM) (p=0.0026). (C) The number of spheroids generated in the untreated cultures (open circle, case 09-148) ranged from 1 to more than 100 for individual duct fragments (mean of 38.7±11; n=14, mean±SEM). Following chloroquine treatment, 12 out of 14 explants did not have any spheroids (mean number of spheroids post treatment 0.21±0.15; n=14; p=0.0049, black circle, mean±SEM). For case 09-301, the mean number of spheroids prior to treatment was 20.5±7.8, n=14 (open triangle, mean±SEM) and there were no spheroids observed after treatment (n=3; black triangle, mean±SEM).
Figure 13B:
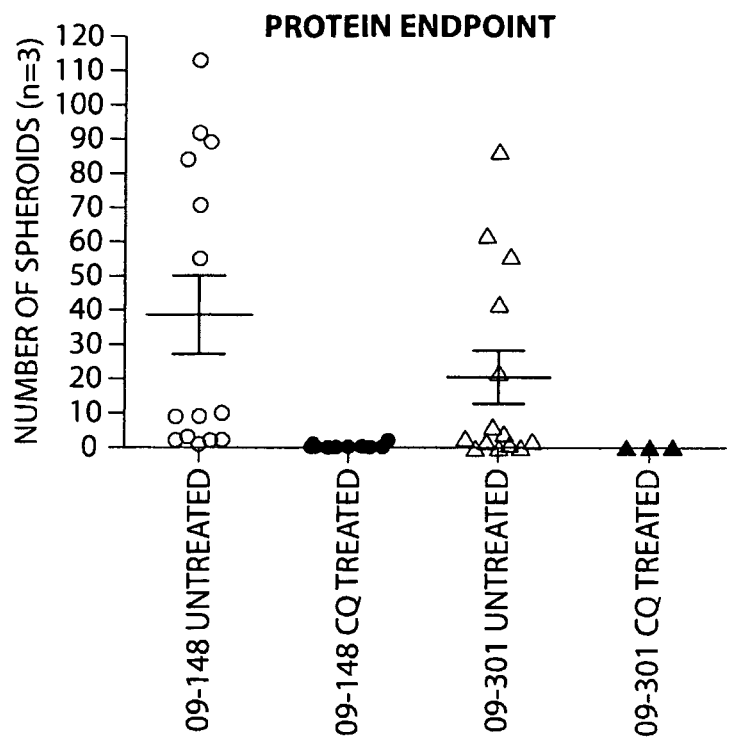

In one embodiment, inhibition of growth or proliferation of the DCIS malignant precursor cells can be determined by counting the number of cells following treatment with a potential therapeutic agent, as compared to untreated cells (FIGS. 13, 14). In another embodiment, the DCIS cells' progenitor potential can be determined by transplanting the cells into a non-human animal as described below.

In another aspect, a method of assessing whether a potential therapeutic agent is useful for the treatment of pre-neoplastic lesions of the breast comprises transplanting a population of DCIS cells of any of the above embodiments to a non-human animal model, administering the potential therapeutic agent to the xenotransplant, and determining whether the therapeutic agent inhibits the growth of the cells, proliferation of the cells or tendency of the cells to grow as tumors, invade or metastasize.

In one embodiment, the potential therapeutic agent may be combined with other substances such as anti-estrogen agents, estrogen binding inhibitors, or estrogen activity inhibitors.

In another, the tendency of the DCIS malignant precursor cells can be determined by examining formed tumors in the non-human animal after a period of time, such as 12 or 24 months, after transplantation. The determination can include a group of non-human animals, each of which is transplanted with an equal size subpopulation of the DCIS malignant precursor cell population, treated or not treated with the potential therapeutic agent. No tumor formulation or a reduced number of tumor formation derived from the transplants indicates that the potential therapeutic agent is useful for the treatment of the pre-neoplastic lesion.

Treatments

In another aspect, methods are provided for preventing or limiting progression of a pre-malignant breast lesion in a patient. Such methods comprise administering to the patient an effective amount of an autophagy inhibitor. In another, methods are provided for treating a patient comprising a pre-malignant breast lesion, comprising administering to the patient an effective amount of an autophagy inhibitor. The pre-malignant breast lesions can comprise a ductal carcinoma in situ (DCIS) malignant precursor cell or an atypical ductal hyperplasia cell.

An autophagy inhibitor refers to any chemical or biological agent that inhibits the activity or suppresses the expression of a gene that positively regulates the autophagy pathway such as, but not limited to, Beclin-1, Atg5, Atg7 or Atg8, or activates the activity or increases the expression of a gent that negatively regulates the autophagy pathway. Non-limiting examples of autophagy inhibitors include chloroquine, hydroxychloroquine, 3-methyladenie, clomipramine, ethyl pyruvate, glycyrrhizin, an agent decreasing the biological activity of one or more of Beclin-1, Atg5, Atg7 or Atg8 and combinations thereof. In one embodiment, the autophagy inhibitor is chloroquine.

The autophagy inhibitors can used alone or in combination with a chemotherapeutic agent. A variety of chemotherapeutic agents are known in the art. Examples include, but are not limited to, cyclophosphamide, doxorubicin, docetaxel, methotrexate, fluorouracil, trastuzumab, tamoxifen, toremifene citrate, lapatinib, axitinib, or pazopanib.

In one aspect, the chemotherapeutic agent is a kinase inhibitor. A variety of kinase inhibitors are known in the art. Examples include, but are not limited to, tamoxifen, toremifene citrate, lapatinib, axitinib, or pazopanib. In one embodiment, the kinase inhibitor is tamoxifen.

Treatment Selection

In another aspect, a method of screening the efficacy of a treatment or selecting a treatment for pre-neoplastic lesions of the breast comprises (A) isolating human breast ductal carcinoma in situ (DCIS) cells from the patient with a method disclosed herein; (B) administering in vitro the potential therapeutic agent to the DCIS cells; (C) culturing the cells; and (D) determining whether the therapeutic agent inhibits the growth of the cells, proliferation of the cells or tendency of the cells to metastasize; and (E) selecting a treatment based upon the determination. In some embodiments, steps (A) to (D) can be repeated after a selected treatment has been administered to the patient. In one embodiment, the potential treatment agent may be combined with other substances such as anti-estrogen agents, estrogen binding inhibitors, or estrogen activity inhibitors.

Treatment Monitoring

In another aspect, a method of monitoring the efficacy of a treatment of a patient with pre-neoplastic lesions of the breast comprises (A) isolating human breast ductal carcinoma in situ (DCIS) cells from the patient with a method disclosed herein; (B) administering in vitro the potential therapeutic agent to the DCIS cells; (C) culturing the cells; and (D) determining whether the therapeutic agent inhibits the growth of the cells, proliferation of the cells or tendency of the cells to invade or grow as tumors. In some embodiments, steps (A) to (D) are performed more than once during the course of treatment.

In one embodiment, the determining step comprises examining the cells in culture conditions, or alternatively by transplanting the cells into a non-human animal to examine the cells' potential to grow, proliferate and metastasize, as described supra.

In one embodiment, the potential therapeutic agent may be combined with other substances such as anti-estrogen agents, estrogen binding inhibitors, or estrogen activity inhibitors.

Embodiments will be further described in the following non-limiting examples.

EXAMPLES

Example 1

Malignant and Invasive Cancer Cells from DCIS Lesions

It has been discovered that human living DCIS lesions contain cells with the ability to grow as invasive tumors in mouse xenografts.

Tumor Transplantation: Breast ductal tissue was incubated with EGF, insulin, and Estrogen in RPMI1640 for 4-12 hours prior to transplantation into the mammary fat pad of NOD/SCID mice (Jackson Labs/Harlan). Tumors that appeared within 2 months of transplantation were excised (Table 1). A portion was saved for in vitro cultivation and the remainder was transplanted for propagation and phenotype analysis.

Results

TABLE 1

Breast xenograft characteristics and tumor generation.

| Mouse ID | Tissue type | ER | PR | Her2 | Xenograft Tumor |
|---|---|---|---|---|---|
| 793 | Breast normal | | | | no |
| 395 | DCIS | | | | yes |

TABLE 1-continued

Breast xenograft characteristics and tumor generation.

| Mouse ID | Tissue type | ER | PR | Her2 | Xenograft Tumor |
|---|---|---|---|---|---|
| 398 | DCIS | | | | yes |
| 581 | DCIS | | | | yes |
| 876 | DCIS | | | | yes |
| 079 | DCIS | Pos (50%) | Pos (50%) | | yes |
| 080 | DCIS | Pos (50%) | Pos (50%) | | yes |
| 081 | DCIS | Pos (50%) | Pos (50%) | | yes |
| 082 | DCIS | Pos (50%) | Pos (50%) | | yes |
| 379/579 | DCIS | | | | yes |
| 396 | DCIS | | | | yes |
| 783/763 | DCIS | Pos (50%) | Pos (50%) | | yes |
| 791 | DCIS | | | | yes |
| 792 | DCIS | Pos (>90%) | Pos (>90%) | | yes |
| 794 | DCIS | | | | no |
| 795 | DCIS | | | | no |
| 528 | DCIS Cell Culture | Pos (50%) | Pos (50%) | | pending |
| 530 | DCIS Cell Culture | Pos (50%) | Pos (50%) | | pending |
| 631 | DCIS Cell Culture | Pos (50%) | Pos (50%) | | yes |
| 632 | DCIS Cell Culture | Pos (50%) | Pos (50%) | | yes |
| 633 | DCIS Cell Culture | Pos (50%) | Pos (50%) | | yes |
| 634 | DCIS Cell Culture | Pos (50%) | Pos (50%) | | yes |
| 635 | DCIS Cell Culture | Pos (50%) | Pos (50%) | | yes |
| 684 | DCIS Cell Culture | Pos (50%) | Pos (50%) | | yes |
| 686 | DCIS Cell Culture | Pos (50%) | Pos (50%) | | no |
| 687 | DCIS Cell Culture | Pos (50%) | Pos (50%) | | no |
| 054 | DCIS pure | Pos (85%) | Neg | | yes |
| 055 | DCIS pure | Pos (>90%) | Pos (30%) | | yes |
| 101 | DCIS pure | Pos (30%) | Neg | | yes |
| 102 | Infiltrating DCIS | | | | no |
| 103 | Infiltrating DCIS | | | | yes |
| 306 | Infiltrating DCIS | | | | no |
| 307 | Infiltrating DCIS | | | | yes |
| 308 | Infiltrating DCIS | | | | no |
| 309 | Infiltrating DCIS | | | | no |
| 310 | Infiltrating DCIS | | | | no |
| 399 | Infiltrating DCIS | | | 3.6 | no |
| 964 | Infiltrating DCIS | | | | no |
| 965 | Infiltrating DCIS | | | | no |
| 396 | Invasive DCIS | | | | yes |
| 301 | Lobular | | | | no |
| 962 | Lobular | | | | yes |
| 963 | Lobular | | | | no |
| 961 | Lobular invasive | | | | no |
| 877 | propagated xenograft DCIS | Pos (30%) | Neg | | yes |
| 051 | propagated xenograft DCIS | | | | yes |
| 391 | propagated xenograft DCIS | | | | yes |
| 392 | propagated xenograft DCIS | | | | yes |
| 395 | propagated xenograft DCIS with IDC | | | | yes |
| 393 | propagated xenograft IDC | | | | no |
| 394 | propagated xenograft pure DCIS | | | | yes |
| 311 | Xenograft culture | | | | no |

Live ductal tissue from nine DCIS lesions were transplanted into NOD/SOD mice. The following aspects were observed: Number of DCIS/IDC cases transplanted: 18 with 43 pieces of tissue transplanted; Number of tumors generated within 3 months: 23; Number of tumors observed for pure DCIS tissue: 18; Tumors observed for mixed DCIS IDC tissue n=5; 7 xenograft propagations yielded 5 tumors for 2 generations from tumor lines derived from pure DCIS. 5/7 xenograft tumors were produced from a primary DCIS tissue cell strain that was in culture for 1-2 months.

Example 2

DCIS Cells Propagated In Vitro

No information exists concerning the existence of tumorigenic/malignant precursor cells within living human pre-invasive lesions such as Ductal Carcinoma in situ (DCIS). It has been discovered, however, that malignant precursor cells exist in DCIS lesions and can propagate in vitro and in vivo (FIGS. 1-4).

Methods

Reverse Phase Protein Array Analysis. Human DCIS breast cells were cultured in minimal medium supplemented with EGF and Insulin in the presence of Streptomycin and Gentamicin. Cells with distinct morphologies were removed by aspiration and mechanical disruption (scraping), spun at 1000 rpm for 5 min, medium was removed and the cell pellet was lysed in TPER, 2× Tris-glycine sample buffer with 10% TCEP Bond Breaker. Reverse phase protein microarrays were printed with an Aushon 2470 arrayer.

Staining and Analysis. Slides were stained with 65 antibodies against phosphorylated proteins involved in pro-survival, growth regulation and apoptosis signaling; antibody binding was visualized using the Catalyzed Signal Amplification Kit (Dako) and diaminobenzidine (DAB). Stained slides were scanned with a flatbed scanner (PowerLook, UMAX) and spot intensities were calculated and normalized using ImageQuant ver5.2 software (GE Healthcare).

Results

This study utilized leftover tissue, not required for diagnosis, obtained at the time of standard of care workup for a suspicious breast lesion. Inclusion criteria are: 1) Female; 2) Diagnosis of pure DCIS or DCIS admixed with Invasive Breast Cancer; 3) A signed consent and adequate sample of primary fresh or frozen tissue; 4) No history of an invasive cancer in the last 5 years with the exception of minimally invasive non-melanoma skin cancer; 5) At least 18 years of age; and 6) Nonpregnant/non-lactating. Exclusion criteria include: 1) Prior history of chemotherapy, hormonal therapy and/or radiation therapy; and 2) History of previous breast surgery in the immediately adjacent area.

In vitro cultivation successfully propagated DCIS derived cells with anchorage independent growth and spheroid formation, in serum free medium supplemented with EGF, insulin.

DCIS intraductal cells that were positive for human specific epithelial antigen were observed to migrate out of the cut open end of DCIS duct organoids grown in culture for as little as 2 weeks. Invading DCIS cells could be documented microscopically in culture (FIGS. 2 and 3). Sub-passage of DCIS cell reconstituted the morphologic phenotypes of tube or duct-like, branching tubes, and spheroid formation.

TABLE 2

Representative cell signaling proteins measured by reverse phase protein microarray.

| Antibody | Function | Antibody | Function | Antibody | Function |
|---|---|---|---|---|---|
| Acetyl-CoA Carboxylase (S79) | Hypoxia/Oxidative stress | Ikappaβ-alpha (S32) | Proteasome Degradation/ Inflammation | 14-3-3 zeta/ gamma/eta | Growth/prosurvival |
| Adducin (S662) | Cytoskeletal regulation | IRS-1 (S612) | Glucose Metabolism | ALDH 1 | Stem cell marker |
| Akt (S473) | Growth/Prosurvival | MEK1/2 (S217/221) | Growth/Prosurvival | Atg5 | Autophagy |
| Akt (T308) | Growth/Prosurvival | Met (Y1234/1235) | Epithelia/ Mesenchymal Transition | Atg12 | Autophagy |
| Arrestin1 (Beta) (S412) (6-24) | Scaffold protein | mTOR (S2448) | Growth/Prosurvival | Beclin-1 | Autophagy |
| ASK1 (S83) | Stress/Inflammation | mTOR (S2481) | Growth/Prosurvival | E-Cadherin | Adhesion |
| ATF-2 (T71) | Transcription factor | NF-kappaβ p65 (S536) | Proteasome Degradation/ Inflammation | CD24 (FL-80) | Stem cell marker |
| ATF-2 (T69/71) | Transcription factor | p70 S6 Kinase (T389) | Growth/Prosurvival | CD44 (156-3C11) | Stem cell marker |
| Bad (S112) | Apoptosis | p70 S6 Kinase (T412) | Growth/Prosurvival | CD133 (W6B3C1) | Stem cell marker |
| Bad (S136) | Apoptosis | p90RSK (S380) | Growth/Prosurvival | Cox-2 (33) | Stress/Inflammation |
| Bad (S155) | Apoptosis | PAK1 (S199/204)/ PAK2 (S192/197) | Cytoskeletal regulation | Cripto | Stem cell marker |
| Bcl-2 (S70) (5H2) | Apoptosis | PAK1 (T423)/PAK2 (T402) | Cytoskeletal regulation | Cytokeratin 8 | Differentiation |
| Bcl-2 (T56) | Apoptosis | PARP, cleaved (D214) | Apoptosis | DKK1 | Adhesion/Differentiation |
| Caspase-3, cleaved (D175) | Apoptosis | Paxillin (Y118) | Adhesion | ErbB2/HER2 | Growth factor receptor |
| Caspase-6, cleaved (D162) | Apoptosis | PDGF Receptor alpha (Y754) | Angiogenesis | ErbB3/HER3 (1B2) | Growth factor receptor |
| Caspase-7, cleaved (D198) | Apoptosis | PDGF Receptor alpha (Y716)) | Angiogenesis | ErbB4/HER4 (111B2) | Growth factor receptor |
| Caspase-9, cleaved (D315) | Apoptosis | PDGF Receptor alpha (Y751) | Angiogenesis | Estrogen Rec alpha | Growth factor receptor |
| Caspase-9, cleaved (D330) | Apoptosis | PKC alpha/beta II (T638/641) | Growth/Prosurvival | Heparanase 1 | Adhesion |
| Catenin (beta) (S33/37/T41) | Adhesion/Differentiation | PLK1 (T210) | Cell Cycle | IL-1beta | Cytokines |
| Catenin (beta) (T41/S45) | Adhesion/Differentiation | PRAS40 (T246) | Cytoskeletal regulation | IL-2 (YNRhIL2) | Cytokines |
| Cofilin (S3) (77G2) | Cytoskeletal regulation | PRK1 (T774)/PRK2 (T816) | Growth/Differentiation | IL-8 | Cytokines |
| EGFR (S1046/1047) | Growth factor receptor | (S190) | Growth factor receptor | LC3B | Autophagy |
| EGFR (Y845) | Growth factor receptor | PTEN (S380) | Tumor suppressor | MMP-9 | Invasion |
| EGFR (Y992) | Growth factor receptor | Pyk2 (Y402) | Migration | MMP-14 | Invasion |
| EGFR (Y1045) | Growth factor receptor | A-Raf (S299) | Growth/Prosurvival | Musashi | Stem cell marker |
| EGFR (Y1068) | Growth factor receptor | B-Raf (S445) | Growth/Prosurvival | Nanog | Stem cell marker |
| EGFR (Y1148) | Growth factor receptor | C-Raf (S338) (56A6) | Growth/Prosurvival | NEDD8 | Ubiquitination/stability |
| EGFR (Y1173) | Growth factor receptor | Ras-GRF1 (S916) | Cytoskeletal regulation | N-Cadherin | Adhesion |
| eIF4E (S209) | Growth/Prosurvival | (S235/236) | Growth/Prosurvival | Nodal | Stem cell marker |
| eIF4G (S1108) | Growth/Prosurvival | Shc (Y317) | Growth/Differentiation | Notch1 | Stem cell marker |
| eNOS (S113) | Hypoxia/Oxidative stress | SHIP1 (Y1020) | Growth/Prosurvival | Osteopontin (OPN) | Adhesion |
| eNOS (S1177) | Hypoxia/Oxidative stress | Smad1/Smad5/Smad8 | Growth/Differentiation | PTEN | Tumor suppressor |
| eNOS/NOS III (S116) | Hypoxia/Oxidative stress | Smad2 (S465/467) | Growth/Differentiation | Skp1 | Ubiquitination/stability |
| ErbB2/HER2 (Y1248) | Growth factor receptor | Smad2 (S245/250/255) | Growth/Differentiation | SUMO-1 | Ubiquitination/stability |
| ErbB3/HER3 (Y1289) (21D3) | Growth factor receptor | Src Family (Y416) | Growth/Differentiation | UBC3 | Ubiquitination/stability |
| ERK 1/2 (T202/Y204) | Growth/Prosurvival | Src (Y527) | Growth/Differentiation | Ubiquitin (P4D1) | Ubiquitination/stability |
| Estrogen Receptor alpha (S118) | Growth factor receptor | Stat1 (Y701) | Stress/Inflammation | Vimentin | Adhesion |
| FADD (S194) | Apoptosis | Stat1 (Y701) | Stress/Inflammation | Wnt3a | Adhesion/Differentiation |
| FAK (Y397) (18) | Adhesion | Stat3 (Y727) | Stress/Inflammation | Wnt5a/b | Adhesion/Differentiation |
| FAK (Y576/577) | Adhesion | Stat3 (Y705) (9E12) | Stress/Inflammation | LRP6 | Adhesion/Differentiation |

TABLE 2-continued

Representative cell signaling proteins measured by reverse phase protein microarray.

| Antibody | Function | Antibody | Function | Antibody | Function |
| --- | --- | --- | --- | --- | --- |
| FKHR (S256) | Cycle cell arrest/Apoptosis | Stat5 (Y694) | Stress/Inflammation | LRP6 Ser1490 | Adhesion/Differentiation |
| FKHRL1 (S253) | Cycle cell arrest/Apoptosis | Stat6 (Y641) | Stress/Inflammation | DV2 | Adhesion/Differentiation |
| FKHR (T24)/FKHRL1 (T32) | Cycle cell arrest/Apoptosis | Tuberin/T5C2 (Y1571) | Adhesion | DV3 | Adhesion/Differentiation |
| GSK-3alpha/beta (S21/9) | Glucose Metabolism | Tyk2 (Y1054/1055) | Stress/Inflammation | Naked 1 | Adhesion/Differentiation |
| GSK-3alpha (Y279)/beta (Y216) | Glucose Metabolism | VEGFR 2 (Y951) | Angiogenesis | Naked 2 | Adhesion/Differentiation |
| IGF-1 Rec (Y1131)/IR (Y1146) | Insulin Receptor | VEGFR 2 (Y996) | Angiogenesis | Axin1 | Adhesion/Differentiation |
| IGF-1R (Y1135/36)/IR (Y1150/51) | Insulin Receptor | VEGFR 2 (Y1175) (19A10) | Angiogenesis | | |

Figure 5:
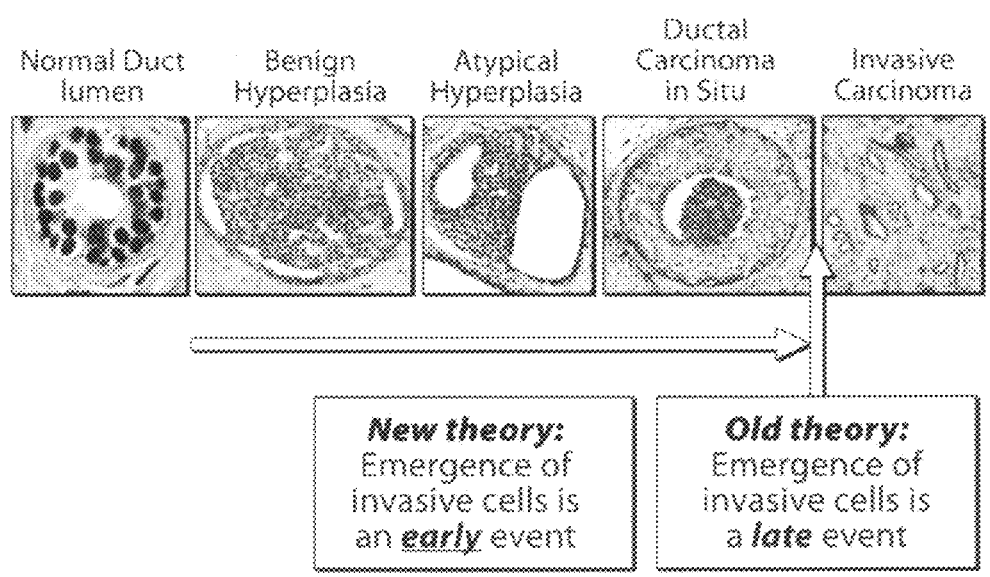
FIG. 5 schematically demonstrates the proposed paradigm shift in the development of breast cancer, that invasive cells emerge early in the tumorigenesis process.

These findings indicate that DCIS contains malignant precursor cells. These novel, isolated DCIS cells provide a model system for reliably generating invasive progenitor cells from fresh human DCIS. This new model provides strategies for understanding breast cancer progression, discovery of DCIS specific prognostic markers, and opportunities for designing rational chemoprevention strategies to arrest breast cancer at the pre-malignant level (FIG. 5).

Figure 4A:
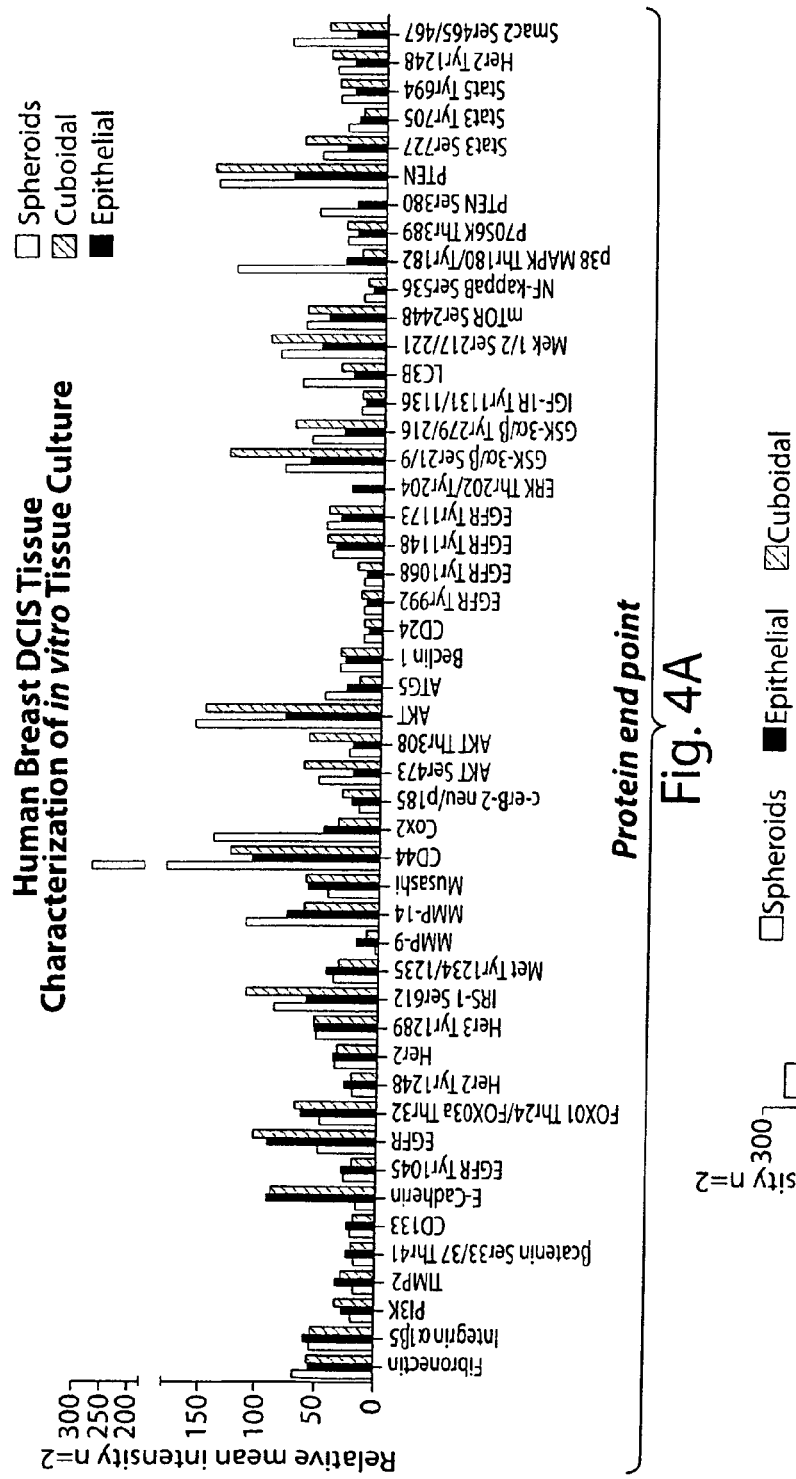
FIG. 4 presents bar charts of RPMA characterization of in vitro cell types cultured from human DCIS tissue that confirms structure and function relationship of spheroids (CD44+, COX2+, MMP-14+, E-Cadherin –), epithelial cells (EGFR+, CD44–, ECadherin+), and cuboidal cells (EGFR+, E-Cadherin+). Expanded view of stem cell marker data in lower panel. The activation state of signaling pathways in the DCIS spheroids was compared to the anchorage dependent cells in organoid culture to phenotypically characterize the cell populations. The 48 endpoints analyzed were total or post-translationally modified proteins for a variety of tyrosine kinase receptors and signaling proteins.
Figure 4B:
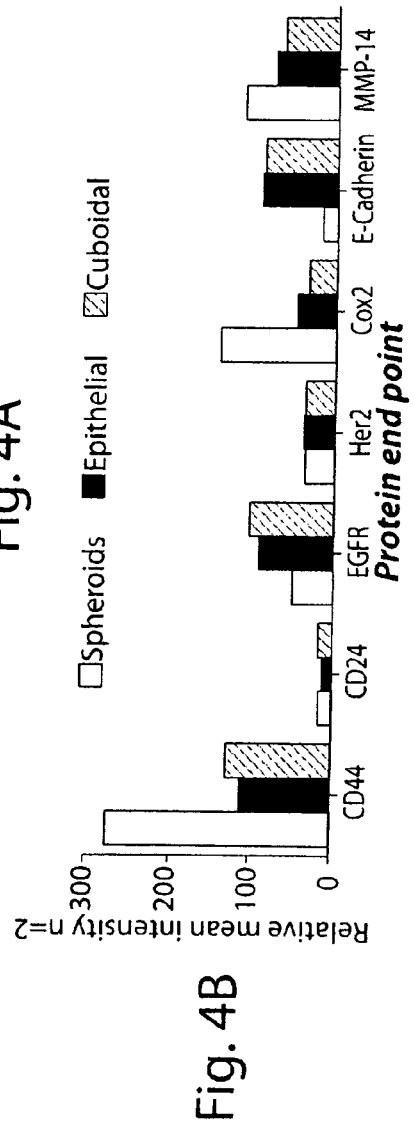
Figure 6:
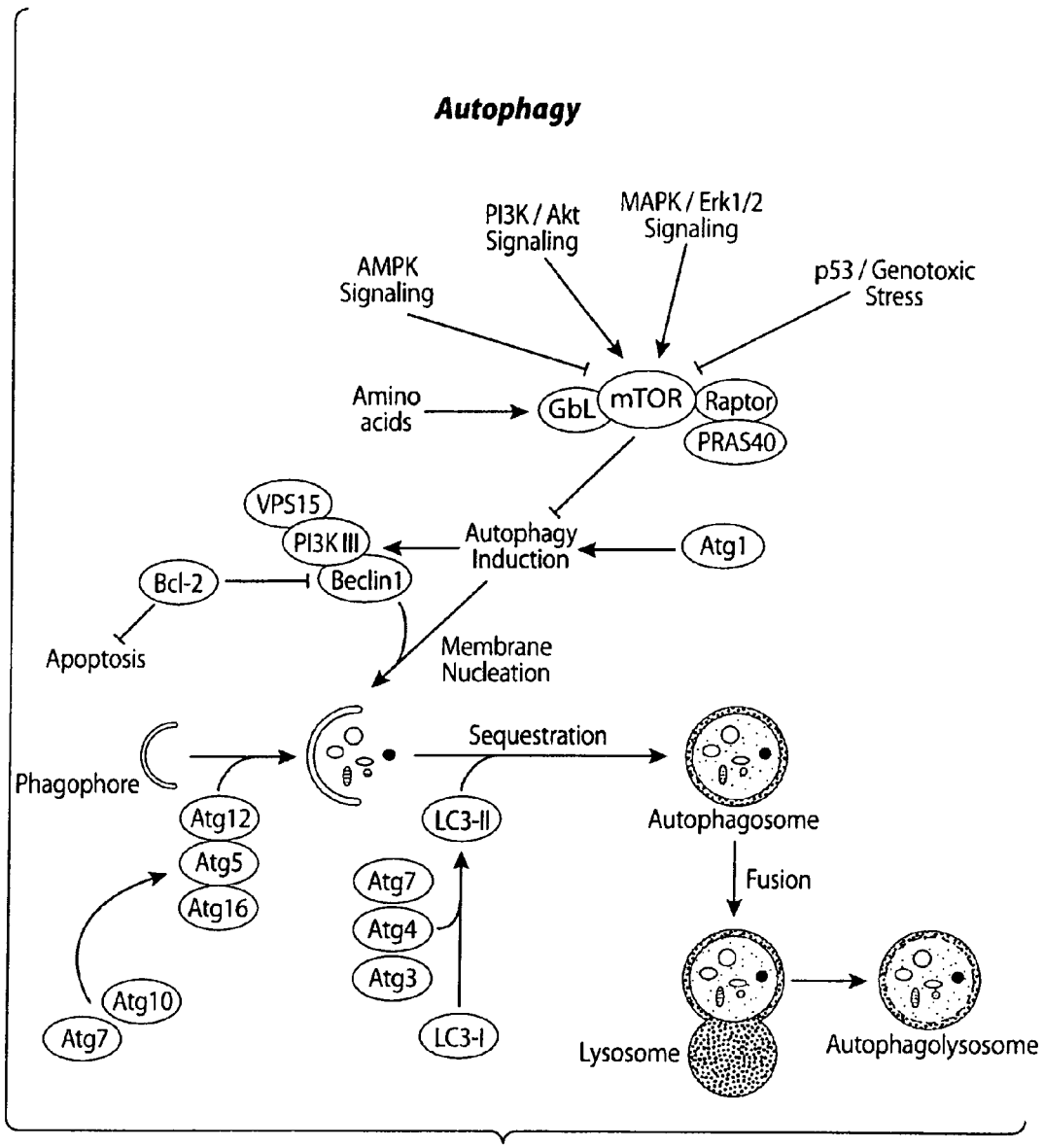
FIG. 6 schematically illustrates the macroautophagy cell signaling pathway. Autophagy (auto—self, phagy—eating) is a catabolic process that can either maintain cellular homeostasis or result in cell death. Intracellular signaling kinases such as AKT, PI3 Kinase, ERK, Bcl-2, and mTOR regulate autophagy. Reverse phase protein microarrays (RPMA) were employed in the present study to evaluate the activation (phosphorylation) of signal pathway proteins that are associated with autophagy.
Figure 7:
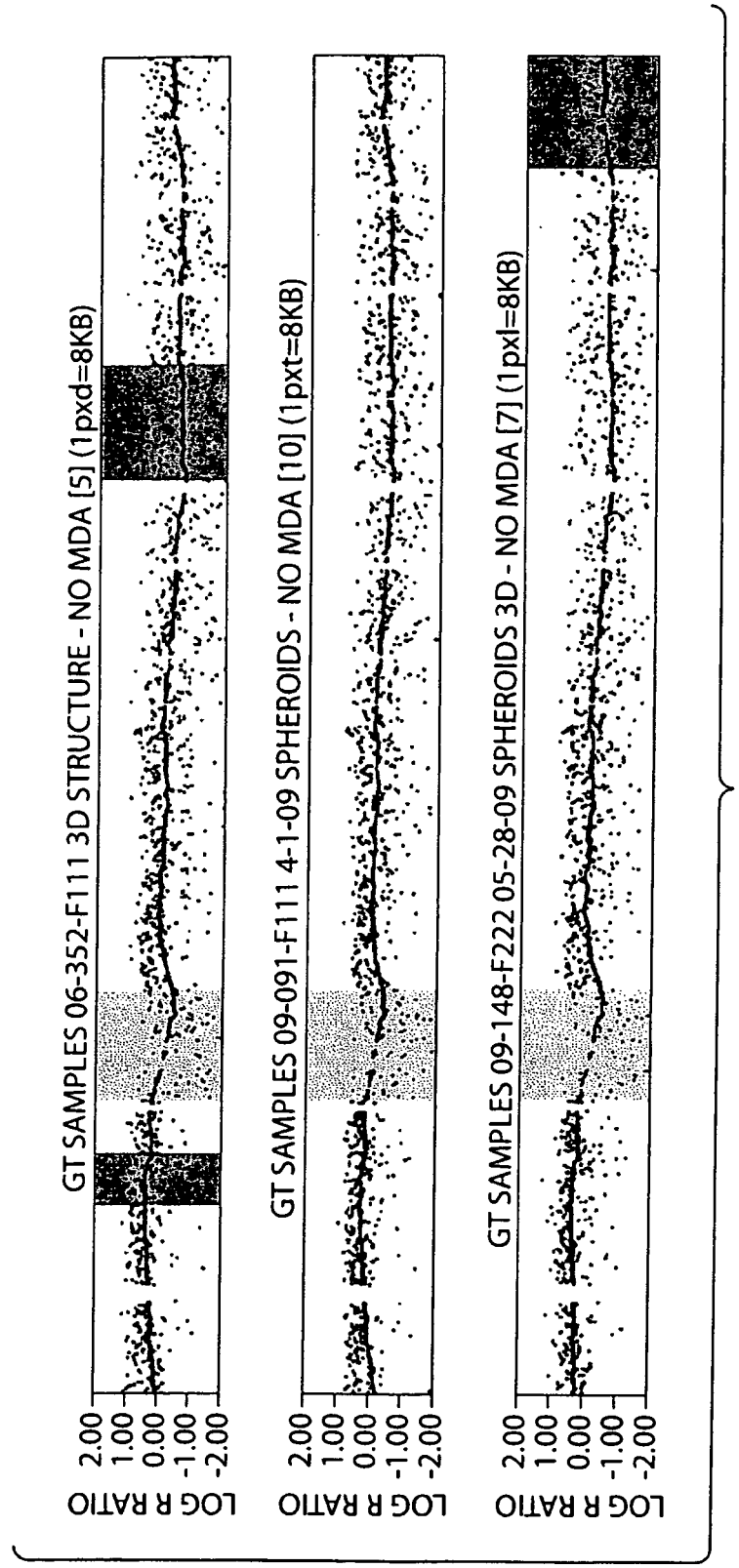
FIG. 7 provides a log R ratio plot showing cultured cells from three different breast DCIS samples that exhibited loss of heterozygosity at a region of chromosome 6p (6p21.1-6p12.3) where the SUPT3H gene is located.
Figure 8:
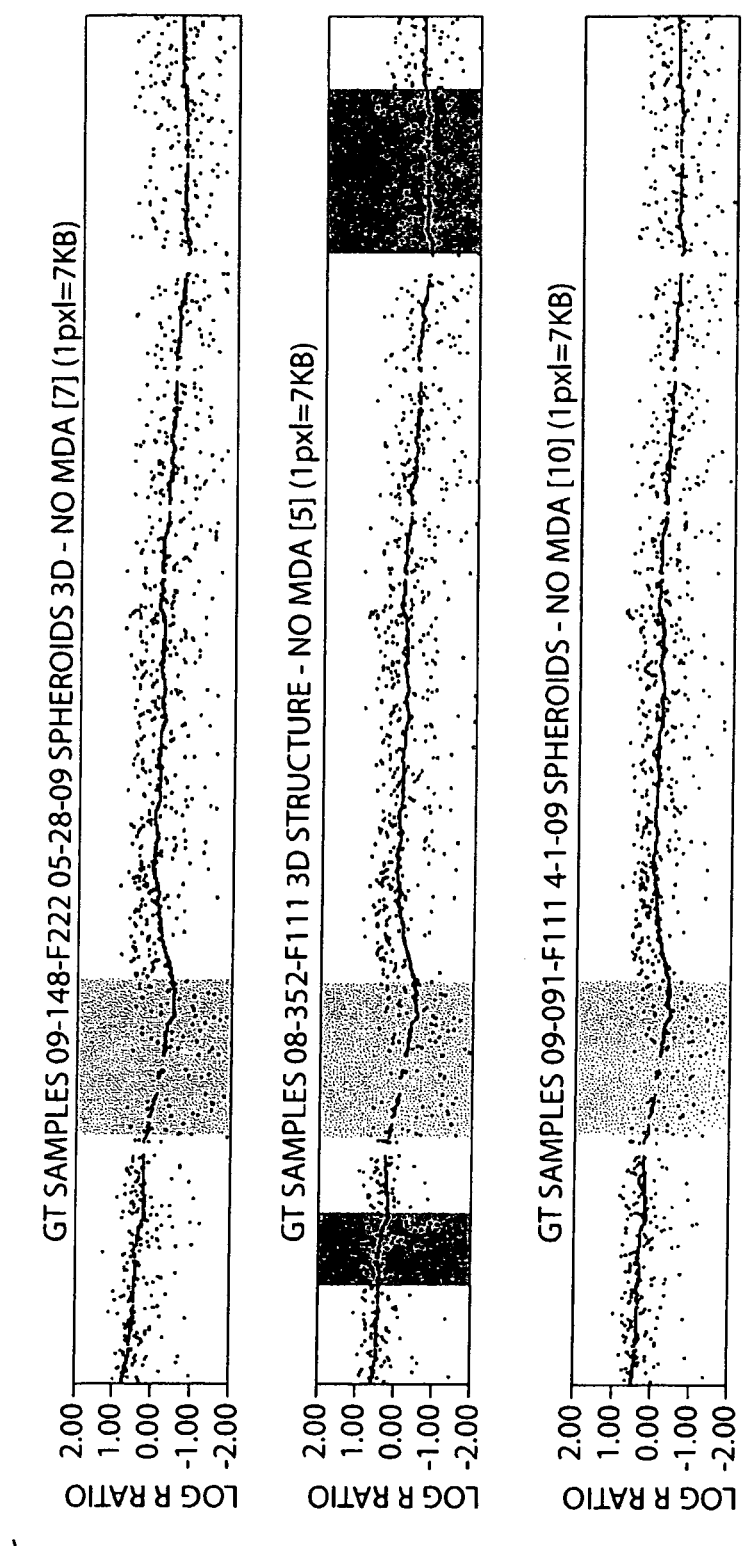
FIG. 8 provides a log R ratio plot showing that molecular karyotype of chromosome 6 from human cultured DCIS cells included a deletion p21.1/12.3. The upper panels show the log R ratio plots from 3 different patients (top: 09-148 spheroids/3-D structure; middle: 08-352 3-D structure; bottom: 09-091 spheroids/3-D structure). These data represent DNA ploidy, or copy number, for the displayed chromosomal region with the horizontal wave line indicating the statistical average value. A log R ratio of 0.0 equals a DNA copy number of 2 (diploid). Deflection downward of the line indicates loss of DNA copy number. Each dot represents the log R ratio value for each SNP. The shaded regions represent segments of DNA deviating from a copy number of 2 as determined by the Illumina Genome Studio 2.0 software. The software uses both quantitative fluorescence intensity and qualitative genotypic data for determining copy number values. The center panel shows the chromosomal ideogram indicating cytological bands with the centromere. The small window shows the region expanded in the figure, and the nucleotide positions for this region are shown below the ideogram. The lower panel shows the cytogenetic bands and genetic map for genes located in the expanded region. Note that the region of the deletion for these 3 patients corresponds to the transcript for SUPT3H.
Figure 8:
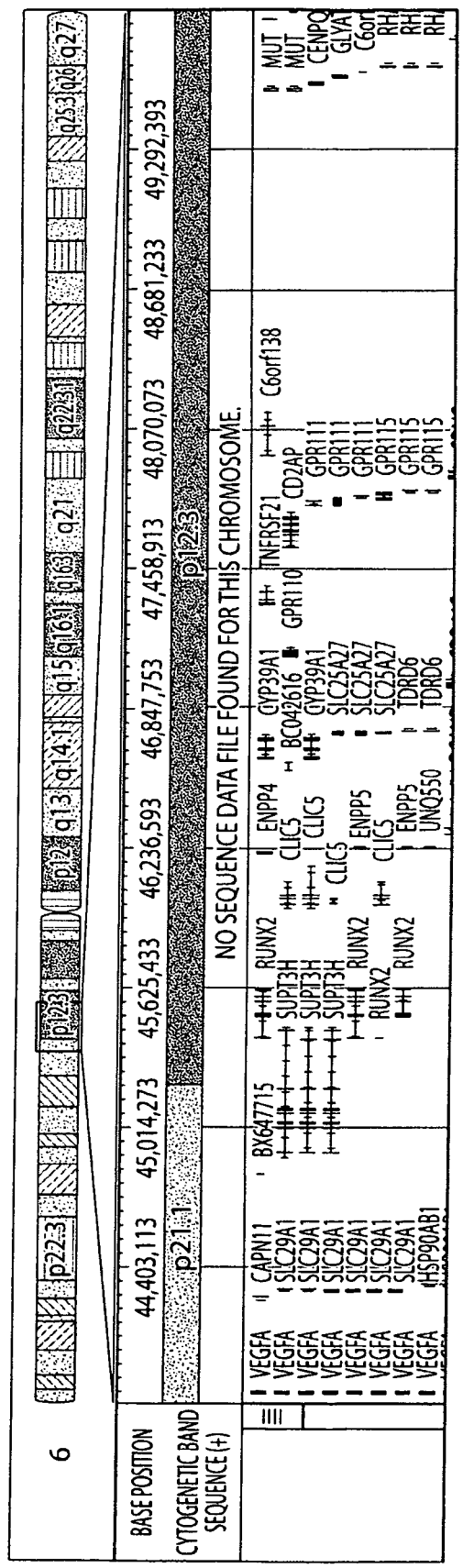
Figure 9:
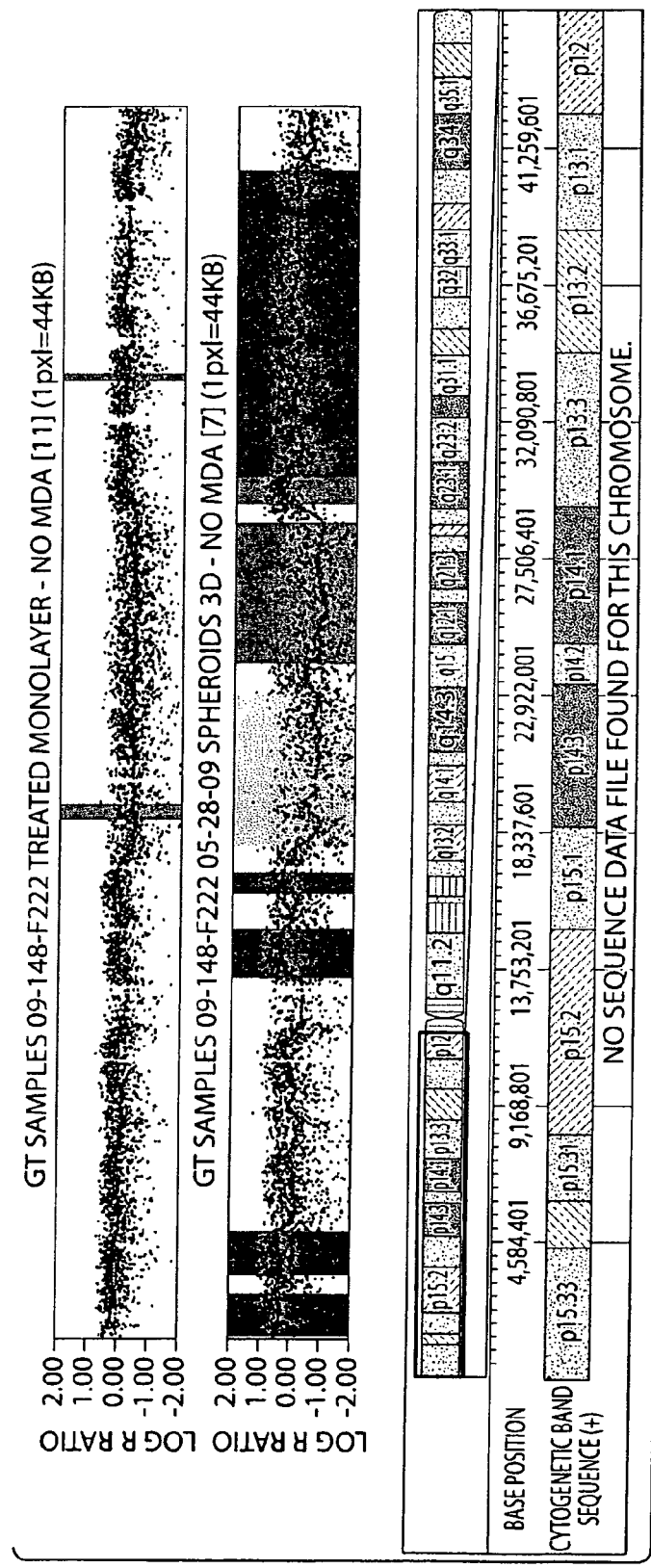
FIG. 9 provides a log R ratio plot showing the molecular karotype of chromosome 5 from chloroquine treated or untreated cultured human DCIS cells. Molecular karyotype of chromosome 5 from chloroquine treated cultured DCIS epithelial monolayer and untreated spheroids. The p-arm shows a gain of copy number. The upper panel shows log 2 ratio plots of 2 different samples from the same patient (top: 09-148 chloroquine treated epithelial monolayer; bottom: 09-148 untreated spheroids/3-D structure). In the upper panel, the top plot shows the log R ratio from chloroquine treated human DCIS cell cultures showing normal ploidy, while the lower plot shows a number of extended regions of gain and loss of content on the p-arm of chromosome 5. Details for the legend are listed above. Additional regions of copy number gain are present distally, including subtelomeric regions. The lower panel shows the cytogenetic banding pattern and the corresponding nucleotide positions beginning with the p-telomere.

Protein array analysis of 48 analyte endpoints (Table 2), representing stem cell markers, autophagy, adhesion, invasion, and prosurvival pathways, revealed a set of activated signaling pathways and markers that were differentially activated in the three morphologies (FIGS. 4, 6). The spheroid cells had higher levels of: CD44, COX2, and MMP-14 compared to anchorage dependent epithelial sheets and lower levels of: CD24 and E-Cadherin compared to anchorage dependent epithelial sheets.

Example 3

Further Testing of the Malignant and Invasive Properties of DCIS Cells

Further testing can be performed to examine the malignant and invasive properties of the DCIS malignant precursor cells, such as in vivo invasion and metastasis testing using xenotransplantation and signaling pathway profiling.

Organ Culture and Microdissection Technology

Organ Culture. Organ cultures consist of isolated cut segments of breast duct organoids less than 5 mm in length that have an exposed duct lumen. The tissue microenvironment is modeled by the addition of adipose tissue and stroma from the local patient donor lesion. The serum free medium is supplemented with insulin, EGF, and Estrogen. In addition, the serum free medium can be supplemented with basement membrane extracts. As shown in Examples 1 and 2, outgrowth of invasive cells can occur in 2 to 4 weeks.

DCIS morphologic subtypes. As described in Examples 1 and 2, the DCIS outgrowths in organ culture have a distinct set of morphologic phenotypes: a migrating front of epithelial sheets, differentiated complex structures, and spheroids (FIGS. 1-3). These morphologic subtypes are recapitulated in subculture in subsequent passages. Moreover, isolates from the different phenotypes maintain tumorigenic potential in mouse xenografts. The morphologic phenotype in culture can be compared with the tumor growth rate pattern, in vivo invasion, and the tumor differentiated histomorphology.

In vivo studies of the invasion phenotype. The invasive phenotype can be studied in vitro using native autologous stroma extracellular matrix invasion barriers or chicken chorioallantoic membrane invasion barriers. Invasion can be judged positive if invading cells are not surrounded by a laminin/type IV collagen basement membrane. Positive invasion can be verified by the presence of human specific epithelial antigen in the invading cells.

Live Tissue Laser Microdissection. Live tissue laser microdissection can be conducted using a combination of laser cutting and laser induced polymer capture of selected organoids. Two classes of lasers can be used: an ultraviolet spectrum laser for cutting and an infrared laser for the capture. A detailed protocol for the instrument, laser focus, power adjustment and polymer support can be found in Espina et al [8], which is incorporated herein by reference. The specimen is oriented on a polymer film. UV laser cutting is used to define the perimeter of the dissection. An infrared laser capture then is used to isolate the desired segment away from the tissue.

Testing invasion and metastasis using xenotransplantation. Intact surgical specimens containing DCIS can be directly transplanted into NOD/SCID mice as previously described for invasive carcinoma cell lines (Example 1). Briefly, freshly obtained surgical specimens can be immediately transferred into organ culture media and held at 37° C. Tissue immediately abutting samples designated for transplant can be sectioned to confirm the presence of DCIS lesions. Tissue samples, morphologic specific isolates from organ culture or microdissected living invading cells for transplantation can be implanted into the mammary fat pad of the mouse. Survival, weight and condition of all mice can be monitored daily, and palpable tumor masses can be measured regularly. Mice exhibiting evidence of tumor growth can be sacrificed as necessary in consultation with a staff veterinarian or after 120 days. Complete necropsy can be performed, and number, size, and location of any metastatic lesions can be noted. Tumors that form from a subset of the DCIS lesions can be passaged into additional NOD/SCID mice for subsequent isolation and propagation of DCIS malignant precursor cells. Tumor masses resulting from transplanted DCIS tissue can be assessed for evidence of vascularization, frankly invasive lesions, and microinvasion. In addition to protein microarray analysis, these specimens can be assessed by immunohistochemistry for subpopulations of cells bearing characteristics of breast cancer stem cells such as: human specific EpCAM, CD44/CD24, cytokeratins 5, 8 and 18, alpha-6 integrin and beta-1 integrin, ALDH1 and Notch1 [7, 13-18].

Proteomic Signal pathway profiling using Reverse Phase Protein Microarrays. Populations of putative DCIS malignant precursor cells from the xenograft and from the ex vivo culture can be microdissected and compared to the same patient's DCIS (described above). The cell populations can be compared with regard to the activation state of protein signal pathways influencing differentiation, survival and apoptosis. Reverse Phase Protein Array Technology [9, 19-23] can be employed to quantify known stem cell markers and to study the Wnt, Notch, Hypoxia, Prosurvival, Apoptosis, Autophagy, and Hormone related signaling pathways relevant to stem cell differentiation [7, 13-18, 24-26]. Reverse phase protein microarrays permit multiplexed analysis of hundreds of proteins and post-translationally modified proteins that are not available by flow cytometry.

Elucidation of functional signaling pathways relevant to the DCIS invasion phenotype ex vivo. Analytes including activated (phosphorylated) signal pathway proteins, stem cell related proteins, and proteins related to motility, prosurvival, autophagy, adhesion, and ECM remodeling can be measured in the cultured cells. Cultured DCIS malignant precursor cell strains can be studied in vitro to assess invasive potential in the presence of specific signal pathway inhibitors. Individual patient DCIS malignant precursor cells can be treated with inhibitors or inducers of erbB receptor kinase, autophagy, prosurvival, and hypoxia related pathways. Continuous strains of DCIS malignant precursor cells can be derived further that retain the invasive phenotype as a future renewable novel system for screening chemoprevention agents that can arrest DCIS malignant precursor cells and prevent the onset of overt malignancy.

Example 4

Figure 15A:
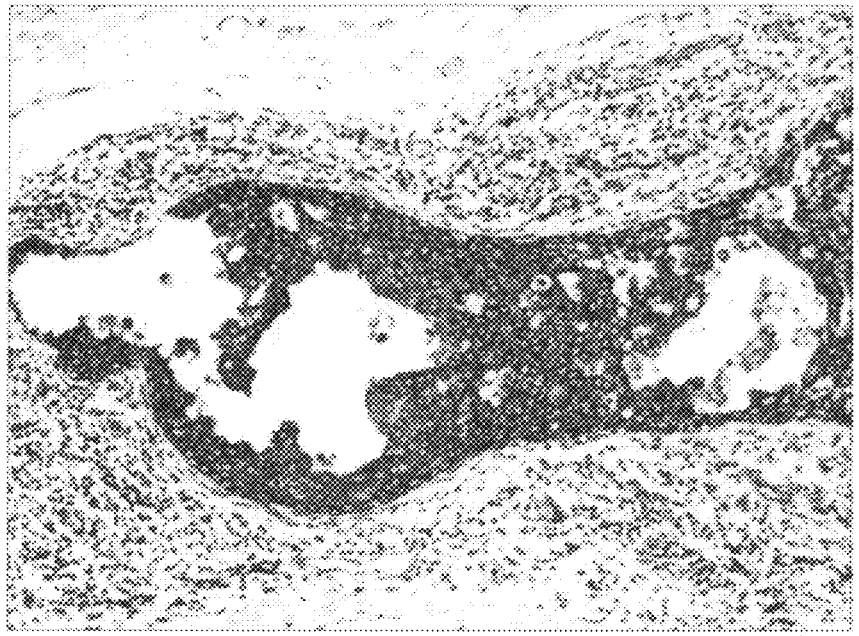
FIG. 15A-B show sub-cellular localization of SUPT3H by immunohistochemistry staining. The SUPT3H gene, located on chromosome 6p in region p21.1 to p12.3, was deleted in the DCIS derived spheroids of three different patients (see FIG. 8). FFPE tissue sections from samples of DCIS with central necrosis were stained with anti-SUPT3H to explore the cell localization of this putative transcription factor in DCIS. Staining is noted in the peri-nuclear membrane zone, as shown by outlining of the nuclei, for a subset of intraductal cells. (A) Case 08-183. (B) Case 08-352, (20×).
Figure 15B:
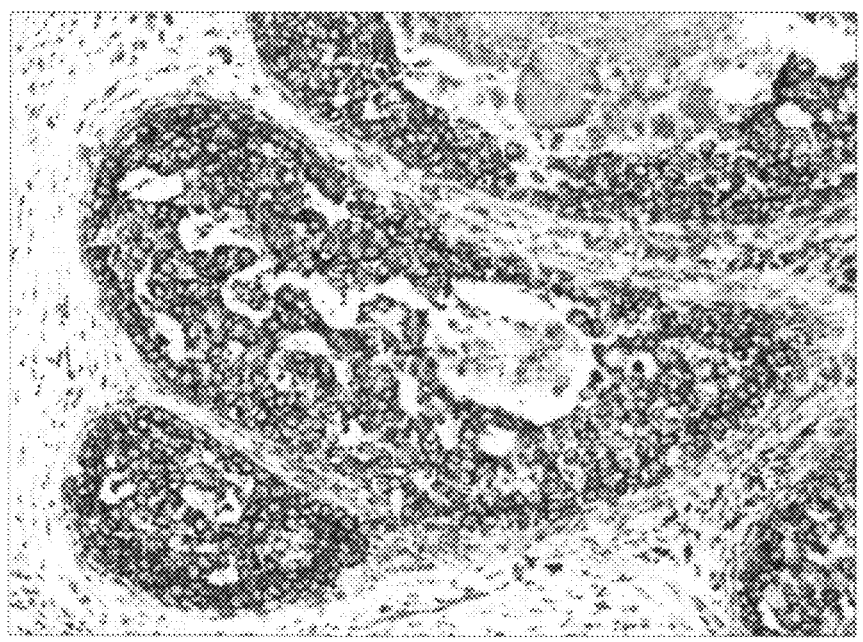

Molecular Cytogenetic Analysis Shows that the DCIS Malignant Precursor Cells are Cytogenetically Abnormal Compared to the Donor Normal Breast Cells Cytogenetic abnormalities have normally been observed in malignant cells. Cells from the DCIS lesions were examined for their cytogenetic abnormalities.
Methods
Molecular Karyotyping. Nucleic acid preparations derived from human breast tissue and/or cell culture out growths were tested for integrity and concentration using quantitative PCR (qPCR) and PicoGreen staining and fluorometry. Microarray-based genomic analysis was performed using CytoSNP-12 beadchips (Illumina, Inc.) and analyzed on an Illumina BeadStation 500 GX laser scanner. The complete microarray protocol required four days using validated SOPs. Briefly, the microarray process involved amplification of the sample's DNA, followed by DNA fragmentation, hybridization of samples to beadchips, single-nucleotide extension, antibody-based labeling, and finally two-color fluorescence scanning and computer-based raw data collection. Raw fluorescence data was converted to genotypic data using the Illumina GenomeStudio software program. Genotypic data output included allele calls (A, C, G, T) for "tagged" single nucleotide polymorphism (SNP) sites and signal intensity values from non-polymorphic sites to determine DNA copy number values. Additionally, data analysis was performed using the Illumina KaryoStudio software program that converts genotypic and signal intensity data into a "molecular karyotype", allowing a cytological display of each chromosome's structure and integrity.
Results
A variety of chromosomal abnormalities including loss or gain in gene copy number was characteristic of the DCIS malignant precursor cells that formed 3-D structures. In three patients a loss of heterozygosity (LOH) is narrowly confined to a region of chromosome 6p (6p21.1-6p12.3) that contains one gene, SUPT3H (Transcription initiation protein SPT3 homolog), was detected in breast DCIS lesions. This LOH is associated with the human breast ductal carcinoma in situ (DCIS) progenitor cell phenotype. Three out of three patient breast tissue culture samples, which exhibited spheroid and 3-D growth in vitro, showed the same LOH region on chromosome 6 (FIGS. 7-10). Antibodies (validated for specificity) to SUPT3H were found to stain, by IHC, the nuclear membrane zone of a subset of intraductal DCIS neoplastic cells (FIG. 15).

Figure 10:
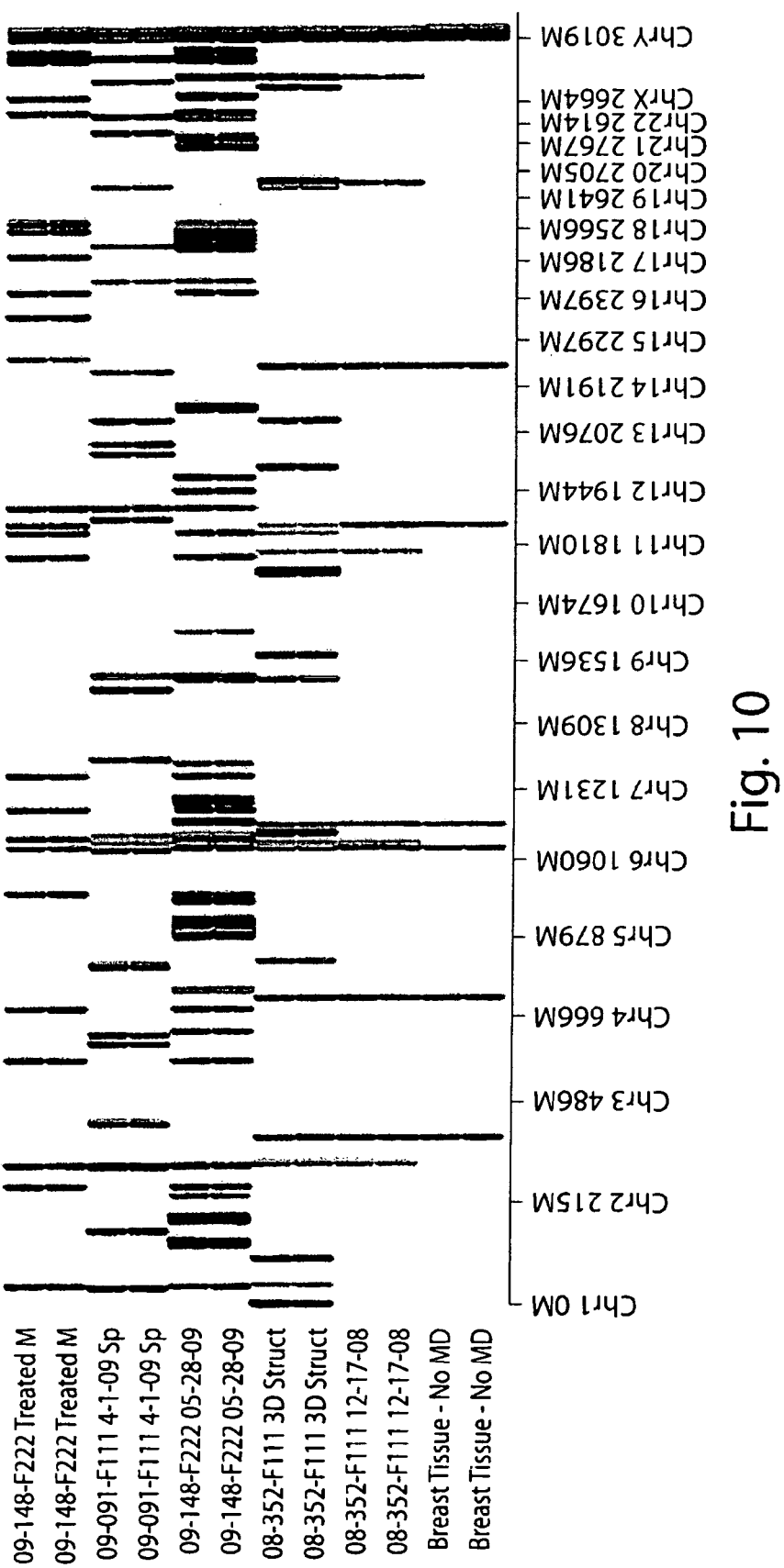
FIG. 10 presents the results of karyotype analysis for human breast DCIS tissue and/or ex vivo cell culture samples. Treated indicates cells were grown in vitro in the presence of Chloroquine 50 mM for >14 days.
Figure 11A:
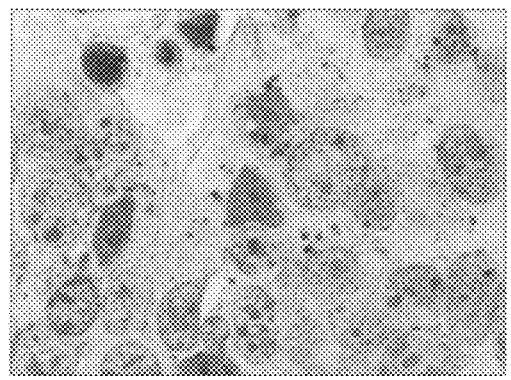
FIG. 11A-F show that autophagy markers are increased in DCIS and can be inhibited with chloroquine. Immunohistochemistry markers for autophagy endpoints were examined in primary DCIS lesions, mouse xenograft tumors, and DCIS ex vivo generated spheroids/pseudoductal structures. Autophagy markers (Atg5, LC3B, Beclin 1) exhibited prominent positive staining in primary human DCIS lesions (Table 4). (A) IHC of a primary DCIS lesion showing punctate staining within the cytoplasm for LC3B a protein associated with autophagosome formation (anti-LC3B, 100×). (B) Beclin1 positive human DCIS derived mouse xenograft tissue (100×). (C-F) Autophagy is also activated in cultured DCIS pseudoductal structures and spheroids. (C) A bright field image of a multi-cellular pseudoductal structure (20×). (D) Fluorescence microscopy shows accumulation of LysoTracker Red dye within the organelles of the inner cell mass of the structure shown in panel C (20×). (E) LysoTracker Red dye accumulation within the central cell mass of a spheroid (red=LysoTracker Red; blue=DAPI nuclear counterstain, 20×). (F) Chloroquine inhibits autophagy by preventing the fusion of autophagosomes and lysosomes in the dynamic, multi-step autophagy cascade. An organoid culture was maintained in culture medium supplemented with chloroquine phosphate (50 µM) for 2 weeks. Dissociation of the spheroid, and diffuse accumulation of LysoTracker Red in autophagic compartments and lysosomes were observed (light gray=LysoTracker Red; dark gray=DAPI nuclear counterstain, 20×, Nikon Eclipse TE200 microscope). Note the granular cytoplasm and cellular swelling.
Figure 11B:
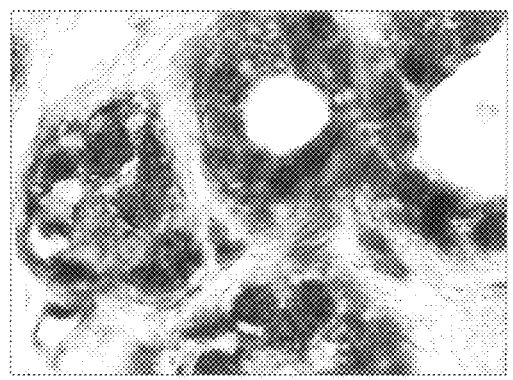
Figure 11C:
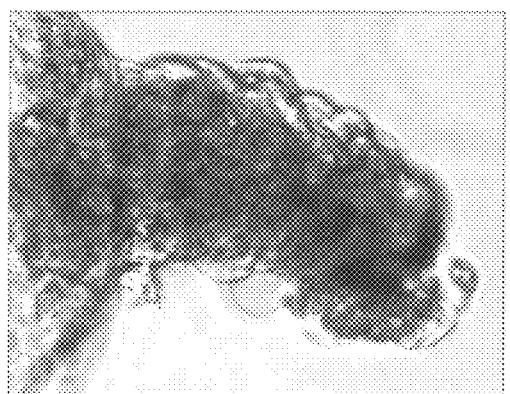
Figure 11D:
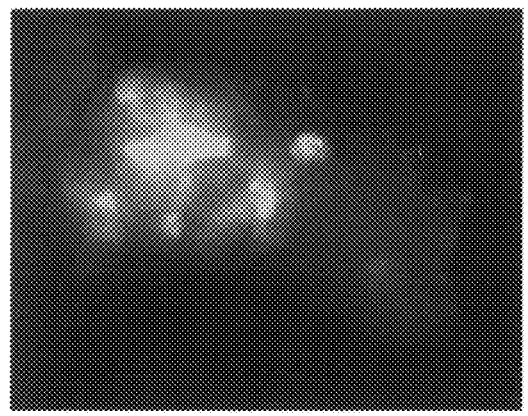
Figure 11E:
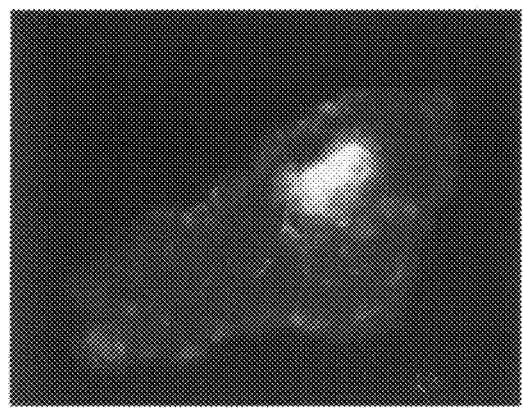
Figure 11F:
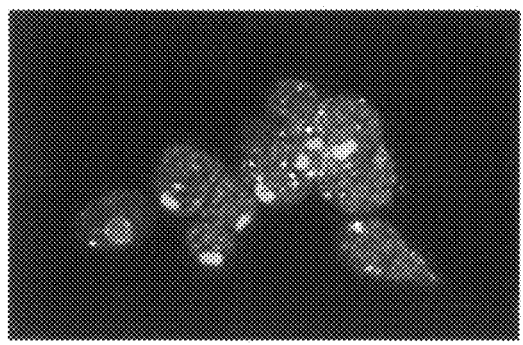

Breast DCIS cells with this abnormal phenotype (i.e., exhibiting a LOH) are prevented from forming out growths (ex vivo) in the presence of Chloroquine (50 mM). Cells treated with Chloroquine (50 mM) did not grow as spheroids or other complex 3-D structures, and these cells did not exhibit chromosome 6p LOH (FIG. 10).

Example 5

Examination of the Role of Autophagy in the Survival of DCIS Malignant Precursor Cells This study considered the role of autophagy in DCIS malignant precursor cell survival in the face of severe metabolic, oxidative, and hypoxic stress.
Materials and Methods
Tissue collection. Fresh, sterile breast DCIS tissue was obtained from patients undergoing standard of care surgery for suspected or biopsy confirmed neoplasia at Inova Fairfax Hospital, Falls Church, Va. Gross tissue pathology at the time of procurement was assessed by a board certified pathologist. Tissue containing DCIS lesions was excised for further macrodissection and rinsed in sterile phosphate buffered saline to remove sentinel lymph node dye. Using sterile technique, ductal tissue was dissected from surrounding breast adipose/fibrous tissue. The ductal tissue was rinsed in serum free DMEM/F12 medium (Invitrogen, Carlsbad, Calif., USA) supplemented with human recombinant EGF (10 ng/mL; Cell Signaling Technology, Danvers, Mass., USA or Millipore, Billerica, Mass., USA), insulin (10 µg/mL; Roche, Indianapolis, Ind., USA), streptomycin sulfate (100 µg/mL; Sigma, St. Louis, Mo., USA) and gentamicin sulfate (20 µg/mL; Sigma) prior to distribution in culture flasks (MidSci, St. Louis, Mo., USA). Ductal tissue was allowed to attach to the culture surface and observed daily for cellular outgrowths. Non-adherent organoids were removed from the culture flask.

Organoid ex vivo culture. Dissected breast ductal tissue was grown in 115 $cm^2$ TPP reclosable flasks (MidSci) or 10 $cm^2$ culture tubes (MidSci) in serum free DMEM/F12 medium supplemented with human recombinant EGF (10 ng/mL), insulin (10 µg/mL), streptomycin sulfate (100 µg/mL) and gentamicin sulfate (20 µg/mL), with or without 0.36% (v/v) murine Engelbreth-Holm-Swarm (EHS) derived, growth factor reduced, basement membrane extract (Trevigen, Gaithersburg, Md., USA) at 37° C. in a humidified 5.0% $CO_2$ atmosphere. Medium was replaced three times per week. Cultures were maintained continuously for up to one year. Periodically, organoids were removed, under microscopic visualization, for propagation into new culture flasks or phenotypic and molecular analysis.

Pharmacological inhibition of autophagy. Autophagy was inhibited in organoid cultures by treating cultures with chloroquine diphosphate (CO) (50 µM-100 µM; Sigma) in DMEM/F12 medium as described above. CO-containing medium was replaced three times per week for a period of 6 months. Comparable untreated control cultures were maintained in identical medium lacking chloroquine with similar media changes.

Immunohistochemistry. Formalin fixed murine tissue or DCIS organoids were processed and paraffin embedded by commercial laboratories (AML Laboratories, Inc, Rosedale, Md. or Bi-Biomics, Nampa, Id.). Formalin fixed paraffin embedded (FFPE) tissue sections (5 μm or 1 μm thickness) mounted on positively charged glass slides were baked at 56° C. for 20 min., deparaffinized in xylene and rehydrated in a series of graded alcohols (100%, 95%, and 70%) with a final rinse in wash buffer (Dako, Carpinteria, Calif., USA). Antigen retrieval, when necessary, was performed with proteinase K or heat induced epitope retrieval. Immunostaining was performed on a Dako Autostainer with an Envision+HRP staining kit (Dako) per manufacturer's instructions. Stained tissue sections were counterstained with Hematoxylin (Dako), rinsed in distilled water and developed in Scott's Tap Water Substitute solution. Cover slips were applied using aqueous mounting medium (Paramount; Dako). Images were captured with an Olympus BX51 microscope using 4×, 10×, 20×, or 100× objectives.

Immunofluorescence and confocal imaging. Spheroids were aspirated directly from the culture flask under direct microscopic visualization, mounted on positively charged glass microscope slides, fixed in 16% paraformaldehyde (Fisher Scientific), and stored dessicated at 4° C. FFPE murine xenograft tissue sections were deparaffinized in xylene, and rehydrated in graded alcohols. Spheroids and FFPE sections were incubated at room temperature with anti-human specific epithelial antigen conjugated to FITC (Ep-CAM-FITC, 5 μg/ml) (Abcam, Cambridge, Mass., USA), or mouse immunoglobulin IgG1 as a negative control (Dako). Slides were rinsed in borate buffer pH 8, then nuclear counterstained with Prolong Gold+DAPI (Invitrogen). Images were captured with a Nikon Eclipse Clsi confocal microscope in different channels for EpCAM-FITC (pseudo-colored green, 488 nm) and DAPI (psuedo-colored blue, 408 nm) using the 20× objective.

Autophagosome lysosome imaging. LysoTracker Red (Invitrogen; 75 nM) and nuclear counterstain Hoechst 33258 pentahydrate (Invitrogen; 5 μg/ml) were added to DMEM/F12 culture medium as described above and incubated with live human DCIS organoid cell cultures for 0.5 hour. Medium containing dye was removed and replaced with fresh medium. Images were captured with either a Nikon Eclipse Clsi confocal or a Nikon Eclipse TE200 microscope in different channels for LysoTracker Red (psuedo-colored red, 561 nm) and Hoechst 33258 (pseudo-colored blue) using either the 10× or 20× objective.

Cell signaling pathway mapping by reverse phase protein microarray (RPMA). Cellular outgrowths were removed from the culture flask by scraping or aspiration with a pipette and spun briefly to pellet the cells. Medium was removed by aspiration and the cell pellet was subjected to lysis with a 10% (v/v) solution of Tris(2-carboxyethyl) phosphine (TCEP; Pierce, Rockford, Ill., USA) in Tissue Protein Extraction Reagent (T-PERTM, Pierce)/2×SDS Tris-glycine 2×SDS buffer (Invitrogen). Cell lysates were stored at −80° C. prior to microarray construction. Cellular lysates were printed on glass backed nitrocellulose array slides (FAST Slides Whatman, Florham Park, N.J.) using an Aushon 2470 arrayer (Aushon BioSystems, Burlington, Mass.) equipped with 350IJm pins as previously described [27]. Cellular lysates prepared from A431±EGF, Hela±Pervanadate, MCF7 (Becton Dickinson, Franklin Lakes, N.J.), SKBR (Santa Cruz Biotechnology) or Jurkat±Calyculin (Cell Signaling Technology) cell lines were printed on each array for quality control assessments. Immunostaining was performed as previously described on a Dako Autostainer per manufacturer's instructions (CSA kit, Dako) [27]. Each slide was incubated with a single primary antibody at room temperature for 30 minutes. Polyclonal and monoclonal antibodies were purchased from Cell Signaling Technology, Abcam, Abnova (Walnut, Calif., USA), Biosource/Invitrogen, BD Biosciences (San Jose, Calif.), Miltenyi (Auburn, Calif., USA), Upstate/Millipore, or Santa Cruz Biotechnology (Santa Cruz, Calif., USA). Antibodies were validated by western blotting as previously described [34]. The negative control slide was incubated with antibody diluent. Secondary antibody was goat anti-rabbit IgG H+L (1:7,500) (Vector Labs, Burlingame, Calif.) or rabbit anti-mouse IgG (1:10) (Dako). Subsequent signal detection was amplified via horseradish peroxidase mediated biotinyl tyramide deposition with chromogenic detection (Diaminobenzidine) per manufacturer's instructions (Dako). Total protein per microarray spot was determined with a Sypro Ruby protein stain (Invitrogen/Molecular Probes) per manufacturer's directions and imaged with a CCD camera (NovaRay, Alpha Innotech, San Leandro, Calif.). Approximately 25 spheroids were analyzed. Data was normalized to β-actin per microarray spot as described in VanMeter et al [34].

Molecular Cytogenetics. Cellular outgrowths were removed from the culture flask by scraping or aspiration with a pipette and were spun briefly to pellet the cells. Culture medium was removed by aspiration, and the cell pellet was immediately frozen on dry ice and stored at −80° C. prior to nucleic acid extraction. Nucleic acid preparations derived from human breast tissue and/or cell culture outgrowths were tested using quantitative PCR (qPCR), PicoGreen (Invitrogen) staining and fluorometry (FLx800 fluorescence plate reader, BioTek, Winooski, Vt., USA). Microarray-based genomic analysis was performed using CytoSNP-12 beadchips (Illumina, Inc., San Diego, Calif., USA) and analyzed on an Illumina BeadStation 500 GX laser scanner [28-30]. Briefly, the microarray process involved sample DNA amplification, followed by DNA fragmentation, hybridization of samples to beadchips, single-nucleotide extension, antibody-based labeling, and finally two-color fluorescence scanning and computer-based raw data collection.

The DNA extraction and purification was performed using a DNA purification column (QIAmp DNA Mini Kit, Qiagen, Valencia, Calif.). Approximately 200 ng of DNA at a concentration of 50 ng/μL was amplified, fragmented, precipitated, re-suspended, and hybridized to the Illumina CytoSNP-12 beadchips. After single-base extension, sample DNA was stained and the chip was washed, dried, and scanned for the resulting 300,000 SNP calls and copy number values. Raw fluorescence data was converted to genotypic data using the Illumina GenomeStudio software program. Genotypic data output included allele calls (A, C, G, T) for "tagged" single nucleotide polymorphism (SNP) sites and signal intensity values from non-polymorphic sites to determine DNA copy number values. Data analysis was performed using the Illumina KaryoStudio software program that converts genotypic and signal intensity data into a "molecular karyotype", allowing a cytological display of each chromosome's structure and integrity.

B allele frequency, Log R ratio, LOH score and Copy Number Score can be measured. In the present analysis, the Log R ratio was examined. The Log R ratio for a sample is the log (base 2) ratio of the normalized R value for the particular SNP divided by the expected normalized R value. The red line in the log R plot indicates a smoothing series with a 200 kb moving average window. Thus, a Log R Ratio\2 was considered to represent a true amplification and Log R Ratio\−1.5 was considered to represent a probable homozygous deletion. Additionally, B allele frequency data was used to identify regions of copy-neutral and hemizygous LOH.

Statistics. The Student T-test, two tailed with Welch's correction, was used to calculate the p-value, and to determine the statistical difference of epithelial outgrowth area before and after CQ treatment. P values <0.05 were considered significant. Standard deviation (SO) or standard error of the mean (SEM) was calculated for group comparisons. Wilcoxon rank sum was used to determine the differences between CQ treated and untreated groups for the reverse phase protein arrays. A p=0.1 was considered different for small sample sizes.

Results

Organoid Culture of Fresh Human DCIS Lesions

Fresh human DCIS tissue was obtained and characterized (Table 3). The tissue was dissected into organoids approximately 3 mm$^2$, containing one or more discernable duct segments with associated stroma. The cut ends of human comedo DCIS lesions could be recognized in the gross specimen by their circular shape and characteristic pale friable center. Organoids that attached to the tissue culture surface were submerged in a minimum volume of medium (just enough to cover the duct fragments) to maximize gas exchange. Submerging the duct segments in a larger volume of media (more than 3 times the height of the fragments) did not yield a successful epithelial outgrowth. Hematoxylin and eosin (H&E) staining of formalin fixed paraffin embedded (FFPE) organoid sections indicated that the organoids contained ducts harboring DCIS, stroma, normal appearing ducts or lobules, and some adipose elements (FIGS. 2 & 3). Histomorphology of the duct fragments revealed, by type IV collagen immunohistochemistry, that intact basement membrane, epithelium and myoepithelium was retained for at least 12 weeks under the culture conditions employed.

Anchorage Independent Neoplastic Epithelial Cells Spontaneously Emerge in Organ Culture of Human DCIS Organoid culture was used to study the nature of the DCIS neoplastic cells that were implicated in tumorigenesis by the xenograft experiments. Migratory proliferative cells that were positive for human specific EpCAM were observed to apparently migrate out of the cut open end of DCIS duct organoids grown in culture for as little as two weeks (within two to four weeks). Continued in vitro organoid cultivation successfully propagated DCIS derived epithelial cells with anchorage independent growth, defined as upward growing and expanding spheroids, and lobulated, duct-like 3-D formations with pseudo lumens, in serum free medium supplemented with EGF and insulin (FIG. 2). Serum free conditions were required; addition of 1% fetal bovine serum caused the epithelial outgrowths to differentiate and degenerate. The culture conditions generated a high yield of DCIS epithelial cell outgrowths. For example, in case 09-301, 39 duct fragments were cultured, 21 attached to the culture flask surface, and 20 generated epithelial outgrowths that generated spheroids and 3-D structures. In case 09-148, 33 duct fragments were cultured, 30 attached, and 19 epithelial outgrowths were generated. For case 09-327 the yield was lower: 17 duct fragments were placed in culture, five attached, and four produced outgrowths. Spheroids and 3-D duct like structure formation did not require suspension in a basement membrane extract (Matrigel™) or collagen gel, although the spheroids were documented to grow and migrate within a growth factor reduced 3-D culture matrix (Trevigen, Gaithersburg, Md.). Neoplastic, (shown below to be cytogenetically abnormal) epithelial cells migrated over the surface of autologous stroma and formed multilayered colonies (FIG. 3). Invasive foci beneath these outgrowths within autologous stroma were verified by absence of type IV collagen basement membrane. Seven human, pure DCIS derived epithelial strains have been propagated and characterized to date, some for as long as one year (Table 3). In seven of seven pure DCIS lesions, the cultured DCIS cells spontaneously generated spheroids or

TABLE 3

Patient characteristics for generation of ex vivo organoid cultures.

| Sample ID | Age | Pathologic Diagnosis | Morphologic subtype | Micro-calcifications | Nuclear Grade | ER | PR | Time in ex vivo culture (months) |
|---|---|---|---|---|---|---|---|---|
| 08-183 | 47 | DCIS | Comedo necrosis/cribriform | Present | 3 | 30% | Neg | 6 |
| 08-352 | 42 | DCIS | Cribriform, extension into lobules with necrosis, no invasive components | Not present | 3 | 50% | 50% | 12 |
| 09-091 | 68 | DCIS/ADH | Cribriform | Present | 2/3 | + | + | 8 |
| 09-118 | 49 | ADH* | Stromal fibrosis with pseudoangiomatoid hyperplasia | Present | 2 | + | N/A | 8 |
| 09-148 | 45 | DCIS | Solid and cribriform type with comedo necrosis | Present | 3 | 90% | 90% | 7 |
| 09-301 | 34 | DCIS | Solid and cribriform type | Not present | 2 | 90% | 90% | 2 |
| 09-327 | 57 | DCIS | Cribriform with necrosis/intraductal papilloma | Present | 2 | + | + | 1 |

DCIS = ductal carcinoma in situ;
ADH = Atypical ductal hyperplasia;
ER = Estrogen Receptor;
PR = Progesterone Receptor;
+ indicates positive result
*Previous history of DCIS, patient treated with Tamoxifen citrate differentiated duct like structures with pseudo lumens. Sub-passage of DCIS organoids reconstituted the 3-D ductal and spheroid phenotypes, which reproducibly invaded inward from the surface of autologous stroma in organoid culture.

Molecular Cytogenetics

Microarray-based genomic analysis was performed using CytoSNP-12 beadchips (Illumina, Inc.) analyzed on an Illumina BeadStation 500 GX laser scanner. Full genotypic data output included allele calls from "tagged" single nucleotide polymorphism (SNP) sites and signal intensity values from non-polymorphic sites to determine DNA copy number values. Molecular cytogenetic profiles demonstrated cytogenetic alterations in the isolated DCIS spheroids (3-5 spheroids per prep) and isolated pseudoductular structures compared to the non-neoplastic, normal karyotype cells in the same patient's DCIS breast tissue. The spheroid abnormal karyotype signature includes loss of copy number on chromosome 5, 6, 8, and 13, and gain of copy number on chromosomes 1, 5, and 17. Abnormalities were present in all DCIS cell spheroids and pseudoductular isolates (FIG. 7-10), but not in the flat epithelial or stromal cells procured from the mixed cell culture. Remarkably, anchorage independent spheroid cells from 3 different patient DCIS lesions all showed narrow copy number loss of chromosome 6 (p21.1/p12.3). This region includes the transcription factor SUPT3H (protein coding GIFtS:59, GC06M044904, UniProtKB/Swiss-Prot: SUPT3_HUMAN, 075486) and other deletions in this region. A second region of aberration was observed in a single patient on the p-arm of chromosome 5 entailing extended regions of gain and loss of chromosomal content. Chromosomal bands from 5p12 to 5p13.3 are present in three copies and a distal segment of 5p13.3 includes four copies. Bands 5p14.1 and 5p14.3 on the same chromosome, however, show loss of DNA content as represented by homozygous and hemizygous deletions, respectively (FIGS. 7-10). The same patient's cultured DCIS cells showed a 14 Megabase (Mb) region of trisomy on chromosome 17, extending from 17q22 to 17q25.1.

Signal Pathway Proteomic Analysis of Cultured Human DCIS Cells

Figure 12A:
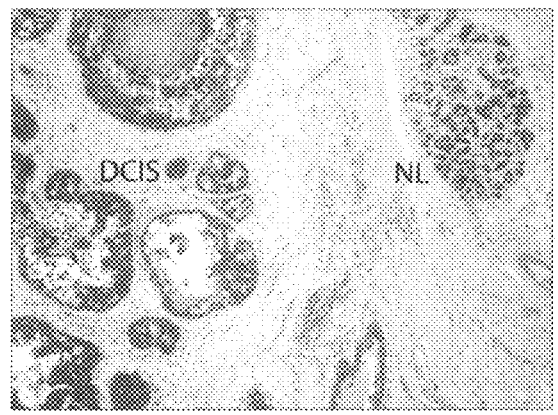
FIG. 12A-C show that autophagy markers are present in primary DCIS lesions and DCIS cultured organoids. (A) Case 08-352 surgical specimen is positive for Atg5 staining in comedo DCIS human breast glands (DCIS) compared to adjacent non-neoplastic ductal elements (NL) (10×). (B-C) Enhanced autophagy marker staining persists in organ culture. (B) Positive Atg5 staining of a DCIS organoid after 12 weeks in culture (20×). (C) DCIS organoid in culture showing glandular and stromal elements with positive staining for Beclin 1 (10×) (Hematoxylin counterstain).
Figure 12B:
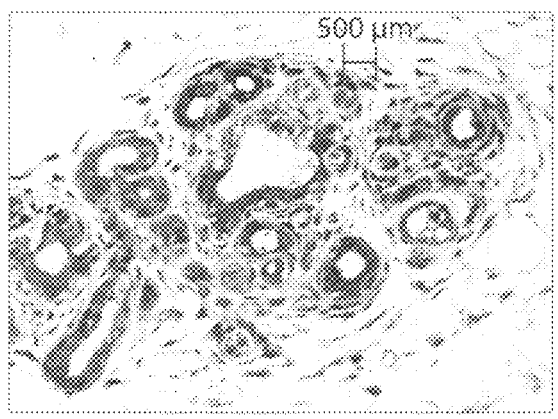
Figure 12C:
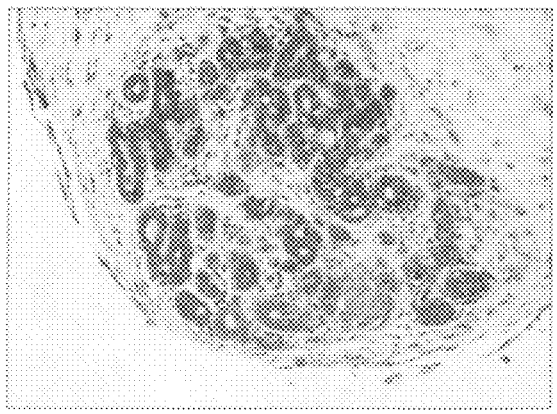

Functional signal pathways for the cultured DCIS cells were examined. Measuring a large number of protein signal pathway endpoints and post-translational modifications by conventional flow cytometry following enzymatic dissociation was not practical, even within a hundred spheroids. Consequently Reverse Phase Protein Microarray (RPMA) analysis of 59 cell signaling kinase endpoints, representing stem cell markers, autophagy, adhesion, invasion, and pro-survival pathways was used. RPMA technology has the required sensitivity and precision for small numbers of cells and provides a means of quantifying phosphoproteins indicative of activated signal pathways [34,35]. Comparison of the spheroids to the flat, single layer epitheloid cells in the same culture revealed a set of activated signaling pathways consistent with a progenitor-type classification. Autophagy markers (Atg5 and LC3B) were elevated in the spheroids in comparison to the epithelial and cuboidal monolayer cells. p38 MAPK Thr180ITyr182 and SMAD2 Ser465/467, cell signaling proteins associated with survival and stress, were elevated in the spheroids in comparison to the epithelial and cuboidal monolayers. The spheroids exhibited progenitor cell characteristics as evidenced by up-regulation of stem cell markers (CD44), down-regulation of cell adhesion markers (E-Cadherin), up-regulation of invasion related metalloproteinases (MMP14), and up-regulation of COX-2 (FIGS. 11-13).

Autophagy Markers Elevated in DCIS Malignant Precursor Cells

Based on the RPMA phenotypic characterization, it was noted that cell signaling pathways intersecting with the autophagy pathway were up-regulated in the cultured DCIS spheroids and 3-D structures. Consequently, the role of autophagy in DCIS was explored using this model system. Autophagy was found to be activated in DCIS lesions in vivo, DCIS cultured organoids, and murine human DCIS xenografts. Intermediate and high-grade DCIS lesions were positive by immunohistochemistry for autophagy pathway proteins Atg5, Beclin-1 and LC3B, which are involved in the nucleation of autophagosomes (Table 4). Autophagosome accumulation, as demonstrated by fluorescence microscopy and immunohistochemistry of endogenous LC3B, showed an increase in punctate LC3B, a hallmark of autophagy because it is the first protein to associate with the autophagosomal membrane (FIGS. 6 and 11) [31,36]. The acidotropic dye, LysoTracker Red (Invitrogen), which accumulates in intracellular organelle components associated with autophagy (autophagosomoses/lysosomes) was used to image live DCIS organoids culture cell outgrowths, including spheroids and 3-D structures. In the DCIS progenitor cells forming spheroids or invading autologous stroma, autophagy was up regulated in the central region of the spheroid as shown by strong fluorescence with LysoTracker Red (FIG. 11) and distinct staining of Atg5 and Beclin-1 by IHC in FFPE tissue sections (FIG. 12 and Table 4).

TABLE 4

Immunohistochemical characterization of primary patient breast tissue.

| Sample ID | Diagnosis | LC3B | Beclin 1 | Atg5 | CD44 | Xenograft tumor generation |
|---|---|---|---|---|---|---|
| 08-183 | DCIS | 1+ | 3+ | 3+ | Positive | Yes |
| 08-352 | DCIS | 1+ | 3+ | 3+ | Positive | Yes |
| 09-091 | DCIS/ADH | 0 | 1+ | 1+ | Negative | Yes |
| 09-118 | ADH* | N/A | 1+ | 1+ | Positive | Yes |
| 09-148 | DCIS | 0 | 2+ | 1+ | Positive | Yes |
| 09-301 | DCIS | 0 | 2+ | 1+ | Positive | pending# |
| 09-327 | DCIS | 0 | 2+ | 1+ | Negative | pending# |

DCIS = ductal carcinoma in situ;
ADH = Atypical ductal hyperplasia
*Previous history of DCIS, patient treated with Tamoxifen citrate.
Tumor growth time has been less than 4 weeks.

Figure 13C:
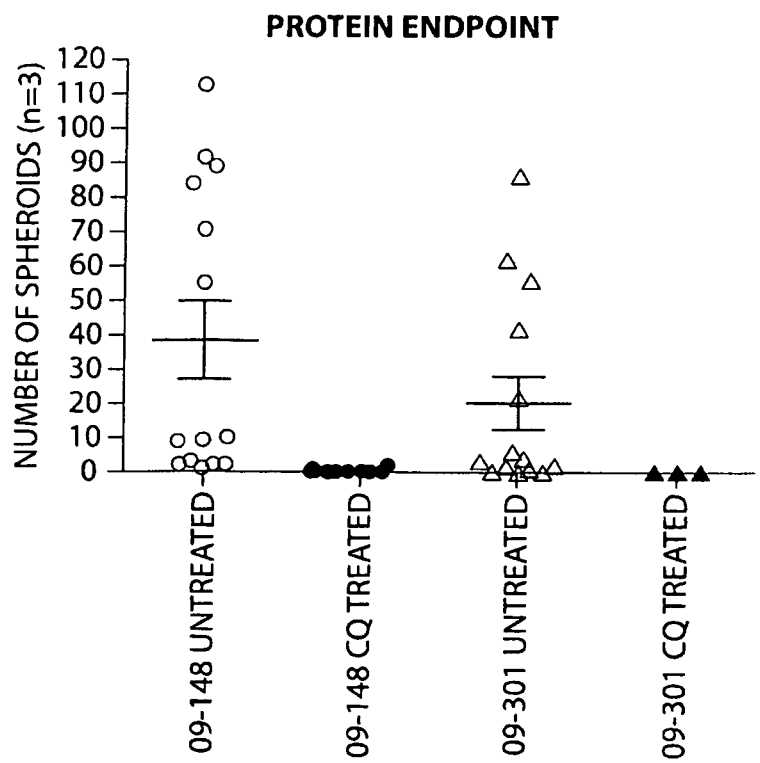
Figure 14A:
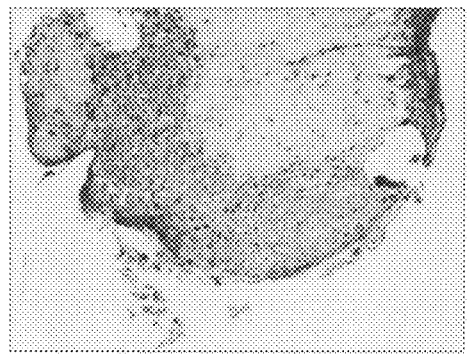
FIG. 14A-D show chloroquine treatment of DCIS organoid cell cultures is associated with cellular degeneration and necrosis. Human breast ductal tissue was allowed to attach to the culture surface and grow in culture for at least 4 weeks prior to treatment with medium containing chloroquine phosphate (50 µM). (A) Degeneration of the invading DCIS cells within the organoid 2 days post chloroquine treatment (10×). (B) DCIS organoid cultured in the presence of chloroquine for 6 months showed complete absence of cellular outgrowths and degenerated cells within the duct (arrow) (10×). (C) Degeneration (arrow) of the multi-layered autologous stromal colony can be compared to the untreated multi-layered growth in FIGS. 3B & D (10×). (D) Cellular swelling and apparent apoptotic death (arrow) of DCIS intraductal epithelial cells within organoid DCIS ductal lesions. (20×) H&E stain of FFPE tissue sections.
Figure 14B:
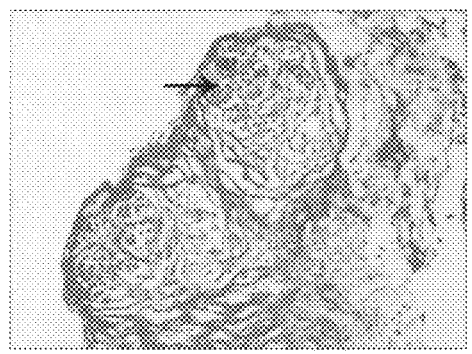
Figure 14C:
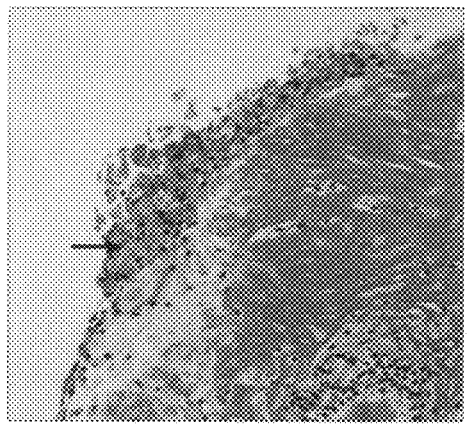
Figure 14D:
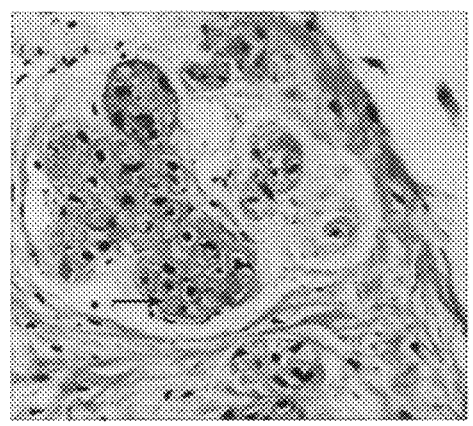

Chloroquine Suppression of Autophagy Causes Regression or Suppression of DCIS Malignant Precursor Cells Treatment of organoids or propagated DCIS epithelial cells with chloroquine phosphate (CQ, Sigma) markedly suppressed outgrowth, spheroid formation, and induced apoptosis (elevation of cleaved PARP Asp214) as early as 48 hours post treatment (FIGS. 13, 14). CQ treatment suppressed autophagy associated signal pathway endpoints in the DCIS malignant precursor cells, including IRS-1 Ser612, AKT Thr308, mTOR Ser2448, ERK Thr2021Tyr204, and p38 Thr180/Tyr182 (FIG. 13A). The remaining adherent cells following CQ treatment displayed lysosomal engorgement (FIG. 14D). For post CQ treated organ cultures examined by cytogenetics, the surviving cells after CQ treatment were found to be cytogenetically normal (FIG. 10). Thus, even in an organoid culture, with a mixed cellular population, the cytogenetically abnormal spheroid forming cells, which emerged within four weeks, were eliminated in the culture by CQ, while the surviving cells retained the normal karyotype of the donor patient tissue. It is believed that CQ treatment blocked the autophagy pathway required for the survival and 3-D growth of the cytogenetically abnormal neoplastic cells. For independent patient DCIS lesions, CQ treatment administered to freshly explanted fragments of ducts prevented any outgrowth of epithelial cells for at least one month and was associated with degeneration of organoid intraductal DCIS epithelial cells. For example for case 09-327, five duct fragments were explanted, and none yielded outgrowths. CQ treatment, administered after outgrowth had occurred for two weeks, markedly suppressed epithelial outgrowth expansion for independent cases (FIG. 13, 14). The mean diameter of the outgrowth prior to treatment was 0.85 cm±0.11 (n=15), and after chloroquine treatment, the mean diameter was (0.084 cm±0.03) (n=23) (p<0.0001). In the second series of organoid cultures, the mean diameter of the outgrowth prior to treatment was 1.36±0.25 (n=8), while the chloroquine treated outgrowth mean diameters was 0.21±0.03 (n=7) (p=0.0026). CQ treatment virtually abolished spheroid and 3-D growth. As shown in FIG. 13C for two different patient DCIS cases, the number of spheroids generated post chloroquine treatment was zero for the majority of explants compared to up to 113 spheroids generated per duct organoid in the untreated culture. The number of spheroids generated in the untreated culture ranged from 1 to more than 100 for individual duct fragments (mean of 38.7±11; n=14). Following chloroquine treatment, 12 out of 14 explants did not have any spheroids (mean number of spheroids post treatment 0.21±0.15; n=14; p=0.0049). CQ treatment of cultured DCIS cells was studied in combination with anti-estrogen compound (tamoxifen) and had a pronounced effect on the inhibition of spheroid outgrowth.

In this example, the model system for ex vivo organoid culture of pure fresh human ductal carcinoma in situ (DCIS) lesions, without enzymatic treatment or sorting, induced the emergence of DCIS malignant precursor cells exhibiting the following characteristics: a) spontaneous generation of hundreds of spheroids and duct-like 3-D structures in culture within 2-4 weeks, b) tumorigenicity in NOD SCID mice, c) cytogenetically abnormal (copy number loss or gain in chromosomes including 1, 5, 6, 8, 13, 17) compared to the normal karyotype of the non-neoplastic cells in the source patient's breast tissue, d) in vitro migration and invasion of autologous breast stroma, and e) up-regulation of signal pathways linked to, and components of, cellular autophagy. Multiple autophagy markers were present in the patient's original DCIS lesion and the mouse xenograft. Treatment with a lysosomotropic inhibitor (chloroquine phosphate) of autophagy completely suppressed the generation of DCIS spheroids/3-D structures, suppressed ex vivo invasion of autologous stroma, induced apoptosis, suppressed autophagy associated proteins including ERK, AKT/PI3 Kinase and mTOR, and eliminated cytogenetically abnormal cells from the organ culture.

There is strong rationale linking autophagy to the survival and invasion of DCIS malignant precursor cells. The first link is hypoxia and nutrient stress [42]. Proliferating ductal epithelial cells accumulating within the breast duct do not have access to the vasculature outside the duct. For this reason, high grade DCIS is associated with central necrosis, and the accumulation of lipofuschin. Autophagy is a pathway activated to promote survival in the face of hypoxic and nutrient stress [32,43-35]. Consequently the activation of autophagy may divert the hypoxic cells away from apoptosis and thereby support the survival and growth of DCIS malignant precursor cells within the lumen [46]. The second link is anoikis, the triggering of apoptotic cell death for cells that have been separated from their normal adhesion substratum [47]. Normal glandular epithelial cells require attachment to, or association with, the basement membrane extracellular matrix (ECM) for continued survival. During ductal hyperplasia and dysplasia epithelial cells exist within the duct at a substantial distance away from association with the peripheral basement membrane. Moreover, invading carcinoma cells can migrate into the stroma in the absence of a basement membrane anchor [48]. Autophagy has been shown to be a key regulator of survival for cells deprived of an anchoring substratum [47], and may play an important role for cell survival in any anchorage independent state. A third link is matrix degradation [44]. High grade DCIS, microinvasion, and overt carcinoma invasion is associated with interruptions, remodeling, and enzymatic breakdown of the basement membrane and the stromal ECM [49,50]. Autophagy may facilitate cell movement through areas of degraded matrix by the phagocytic processing of matrix breakdown fragments [51]. A fourth link is calcium. Microcalcifications are mammographic indicators of high grade DCIS [52], and calcium phosphate precipitates are potent inducers of autophagy [53]. Based on these established mechanistic roles, autophagy constitutes a novel target for treating DCIS and arresting DCIS transition to overt invasion.

Chloroquine phosphate, which suppressed or abolished the DCIS malignant precursor cells, is an orally administered small molecule inhibitor which blocks the autophagy pathway by accumulating in autophagosomes and inhibiting autophagosomal formation/function. Anti-autophagy therapy can be combined with other agents. Chloroquine or any direct or indirect inhibitor of autophagy constitutes a treatment for premalignant breast cancer.

REFERENCES

1. Li, C. I., Malone, K. E., Saltzman, B. S., Daling, J. R., Risk of invasive breast carcinoma among women diagnosed with ductal carcinoma in situ and lobular carcinoma in situ, 1988-2001. *Cancer* 2006, 106, 2104-12.
2. Li, C. I., Daling, J. R., Malone, K. E., Age-specific incidence rates of in situ breast carcinomas by histologic type, 1980 to 2001. *Cancer Epidemiol Biomarkers Prev* 2005, 14, 1008-11.
3. Leonard, G. D., Swain, S. M., Ductal carcinoma in situ, complexities and challenges. *J Natl Cancer Inst* 2004, 96, 906-20.
4. Hu, M., Yao, J., Carroll, D. K., Weremowicz, S. et al., Regulation of in situ to invasive breast carcinoma transition. *Cancer Cell* 2008, 13, 394-406.
5. Lagios, M. D., Heterogeneity of duct carcinoma in situ (DCIS): relationship of grade and subtype analysis to local recurrence and risk of invasive transformation. *Cancer Lett* 1995, 90, 97-102.
6. Collins, L. C., Tamimi, R. M., Baer, H. J., Connolly, J. L. et al., Outcome of patients with ductal carcinoma in situ untreated after diagnostic biopsy: results from the Nurses' Health Study. *Cancer* 2005, 103, 1778-84.
7. Ma, X. J., Dahiya, S., Richardson, E., Erlander, M. et al., Gene expression profiling of the tumor microenvironment during breast cancer progression. *Breast Cancer Res* 2009, 11, R7.
8. Espina, V., Wulfkuhle, J. D., Calvert, V. S., VanMeter, A. et al., Laser-capture microdissection. *Nat Protoc* 2006, 1, 586-603.
9. VanMeter, A. J., Rodriguez, A. S., Bowman, E. D., Jen, J. et al., Laser capture microdissection and protein microarray analysis of human non-small cell lung cancer: differential epidermal growth factor receptor (EGPR) phosphorylation events associated with mutated EGFR compared with wild type. *Mol Cell Proteomics* 2008, 7, 1902-24.

10. Beckhove, P., Schutz, F., Diel, I. J., Solomayer, E. F. et al., Efficient engraftment of human primary breast cancer transplants in nonconditioned NOD/Scid mice. *Int J Cancer* 2003, 105, 444-53.
11. Al-Hajj, M., Wicha, M. S., Benito-Hernandez, A., Morrison, S. J. et al., Prospective identification of tumorigenic breast cancer cells. *Proc Natl Acad Sci USA* 2003, 100, 3983-8.
12. Visonneau, S., Cesano, A., Torosian, M. H., Miller, E. J. et al., Growth characteristics and metastatic properties of human breast cancer xenografts in immunodeficient mice. *Am J Pathol* 1998, 152, 1299-311.
13. Dontu, G., Jackson, K. W., McNicholas, E., Kawamura, M. J. et al., Role of Notch signaling in cell-fate determination of human mammary stem/progenitor cells. *Breast Cancer Res* 2004, 6, R605-15.
14. Ginestier, C., Hur, M. H., Charafe-Jauffret, E., Monville, F. et al., ALDH1 is a marker of normal and malignant human mammary stem cells and a predictor of poor clinical outcome. *Cell Stem Cell* 2007, 1, 555-67.
15. Hu, M., Peluffo, G., Chen, H., Gelman, R. et al., Role of COX-2 in epithelial-stromal cell interactions and progression of ductal carcinoma in situ of the breast. *Proc Natl Acad Sci USA* 2009, 106, 3372-7.
16. Kulkarni, S., Patil, D. B., Diaz, L. K., Wiley, E. L. et al., COX-2 and PPARgamma expression are potential markers of recurrence risk in mammary duct carcinoma in-situ. *BMC Cancer* 2008, 8, 36.
17. Liu, S., Dontu, G., Mantle, I. D., Patel, S. et al., Hedgehog signaling and Bmi-1 regulate self-renewal of normal and malignant human mammary stem cells. *Cancer Res* 2006, 66, 6063-71.
18. Stingl, J., Eaves, C. J., Kuusk, U., Emerman, J. T., Phenotypic and functional characterization in vitro of a multipotent epithelial cell present in the normal adult human breast. *Differentiation* 1998, 63, 201-13.
19. Espina, V., Mehta, A. I., Winters, M. E., Calvert, V. et al., Protein microarrays: molecular profiling technologies for clinical specimens. *Proteomics* 2003, 3, 2091-100.
20. Iyengar, P., Espina, V., Williams, T. W., Lin, Y. et al., Adipocyte-derived collagen VI affects early mammary tumor progression in vivo, demonstrating a critical interaction in the tumor/stroma microenvironment. *J Clin Invest* 2005, 115, 1163-76.
21. Liotta, L. A., Espina, V., Mehta, A. I., Calvert, V. et al., Protein microarrays: meeting analytical challenges for clinical applications. *Cancer Cell* 2003, 3, 317-25.
22. Paweletz, C. P., Charboneau, L., Bichsel, V. E., Simone, N. L. et al., Reverse phase protein microarrays which capture disease progression show activation of pro-survival pathways at the cancer invasion front. *Oncogene* 2001, 20, 1981-9.
23. Wulfkuhle, J. D., Speer, R., Pierobon, M., Laird, J. et al., Multiplexed cell signaling analysis of human breast cancer applications for personalized therapy. *J Proteome Res* 2008, 7, 1508-17.
24. Huang, E. H., Hynes, M. J., Zhang, T., Ginestier, C. et al., Aldehyde dehydrogenase 1 is a marker for normal and malignant human colonic stem cells (SC) and tracks SC overpopulation during colon tumorigenesis. *Cancer Res* 2009, 69, 3382-9.
25. Kalirai, H., Clarke, R. B., Human breast epithelial stem cells and their regulation. *J Pathol* 2006, 208, 7-16. Docket No. GMU-09-043P2 Page 18 of 19
26. Smalley, M., Ashworth, A., Stem cells and breast cancer: A field in transit. *Nat Rev Cancer* 2003, 3, 832-44.
27. Espina V, Edmiston K H, Heiby M, Pierobon M, Sciro M, et al (2008) A portrait of tissue phosphoprotein stability in the clinical tissue procurement process. *Mol Cell Proteomics* 7: 19982018.
28. Mardis E R (2008) The impact of next-generation sequencing technology on genetics. *Trends Genet.* 24: 133-141.
29. Smith D R, Quinlan A R, Peckham H E, Makowsky K, Tao W, et al (2008) Rapid whole genome mutational profiling using next-generation sequencing technologies. *Genome Res* 18: 1638-1642.
30. Rao S K, Edwards J, Joshi A D, Siu I M, Riggins G J (2009) A survey of glioblastoma genomic amplifications and deletions. *J Neurooncol.* 2009 Jul. 17. [Epub ahead of print]
31. Klionsky D J, Abeliovich H, Agostinis P, Agrawal D K, Aliev G, et al (2008) Guidelines for the use and interpretation of assays for monitoring autophagy in higher eukaryotes. *Autophagy* 4: 151-175.
32. Vazquez-Martin A, Oliveras-Ferraros C, Menendez J A (2009) Autophagy facilitates the development of breast cancer resistance to the anti-HER2 monoclonal antibody trastuzumab. *PLoS One* 4: e6251.
33. Beckhove P, Schutz F, Diel I J, Solomayer E F, Bastert G, et al (2003) Efficient engraftment of human primary breast cancer transplants in nonconditioned NOD/Scid mice. *Int J Cancer* 105: 444-453.
34. VanMeter A J, Rodriguez A S, Bowman E D, Jen J, Harris C C, et al (2008) Laser capture microdissection and protein microarray analysis of human non-small cell lung cancer: differential epidermal growth factor receptor (EGPR) phosphorylation events associated with mutated EGFR compared with wild type. *Mol Cell Proteomics* 7: 1902-1924.
35. Paweletz C P, Charboneau L, Bichsel V E, Simone N L, Chen T, et al (2001) Reverse phase protein microarrays which capture disease progression show activation of pro-survival pathways at the cancer invasion front. *Oncogene* 20: 1981-1989.
36. Gao W, Kang J H, Liao Y, Ding W X, Gambotto A A, et al (2010) Biochemical isolation and characterization of the tubulovesicular LC3-positive autophagosomal compartment. *J Biol. Chem.* 285(2):1371-83.
37. Redon R, Ishikawa S, Fitch K R, Feuk L, Perry G H, et al (2006) Global variation in copy number in the human genome. *Nature* 444: 444-454.
38. Sebat J, Lakshmi B, Troge J, Alexander J, Young J, et al (2004) Large-scale copy number polymorphism in the human genome. *Science* 305: 525-528.
39. Gamper A M, Roeder R G (2008) Multivalent binding of p53 to the STAGA complex mediates coactivator recruitment after UV damage. *Mol Cell Biol* 28: 2517-2527.
40. Liu X, Vorontchikhina M, Wang Y L, Faiola F, Martinez E (2008) STAGA recruits Mediator to the MYC oncoprotein to stimulate transcription and cell proliferation. *Mol Cell Biol* 28: 108-121.
41. Martinez E, Palhan V B, Tjemberg A, Lymar E S, Gamper A M, et al (2001) Human STAGA complex is a chromatin-acetylating transcription coactivator that interacts with pre-mRNA splicing and DNA damage-binding factors in vivo. *Mol Cell Biol* 21: 6782-6795.
42. Gozuacik D, Kimchi A (2007) Autophagy and cell death. *Curr Top Dev Biol* 78: 217-245.
43. Schoenlein P V, Periyasamy-Thandavan S, Samaddar J S, Jackson W H, Barrett J T (2009) Autophagy facilitates the progression of ERalpha-positive breast cancer cells to anti-estrogen resistance. *Autophagy* 5: 400-403.

44. Scarlatti F, Granata R, Meijer A J, Codogno P (2009) Does autophagy have a license to kill mammalian cells? *Cell Death Differ* 16: 12-20.
45. Maiuri M C, Tasdemir E, Criollo A, Morselli E, Vicencio J M, et al (2009) Control of autophagy by oncogenes and tumor suppressor genes. *Cell Death Differ* 16: 87-93.
46. Schafer Z T, Grassian A R, Song L, Jiang Z, Gerhart-Hines Z, et al (2009) Antioxidant and oncogene rescue of metabolic defects caused by loss of matrix attachment. *Nature* 461: 109113.
47. Fung C, Lock R, Gao S, Salas E, Debnath J (2008) Induction of autophagy during extracellular matrix detachment promotes cell survival. *Mol Biol Cell* 19: 797-806.
48. Liotta L A, Tryggvason K, Garbisa S, Hart I, Foltz C M, et al (1980) Metastatic potential correlates with enzymatic degradation of basement membrane collagen. *Nature* 284: 67-68.
49. Jedeszko C, Victor B C, Podgorski I, Sloane B F (2009) Fibroblast hepatocyte growth factor promotes invasion of human mammary ductal carcinoma in situ. *Cancer Res* 69: 9148-9155.
50. Iyengar P, Espina V, Williams T W, Lin Y, Berry D, et al (2005) Adipocyte-derived collagen VI affects early mammary tumor progression in vivo, demonstrating a critical interaction in the tumor/stroma microenvironment. *Clin Invest* 115: 1163-1176.
51. Lock R, Debnath J (2008) Extracellular matrix regulation of autophagy. *Curr Opin Cell Biol.* 20: 583-588.
52. de Roos M A, van der Vegt B, de Vries J, Wesseling J, de Bock G H (2007) Pathological and biological differences between screen-detected and interval ductal carcinoma in situ of the breast. *Ann Surg Oncol* 14: 2097-2104.
53. Gao W, Ding wx., Stolz D B, Yin X M (2008) Induction of macroautophagy by exogenously introduced calcium. *Autophagy* 4: 754-761.

What is claimed is:

1. An isolated population of living human breast ductal carcinoma in situ (DCIS) cells treated in an artificial serum free culture media comprising buffered salts, epidermal growth factor and insulin, wherein the cells (i) are epithelial in origin, (ii) comprise one or more markers of autophagy, (iii) show at least one genetic difference from normal cells, (iv) form 3-D spheroids or duct-like structures or ball aggregates without enzymatic digestion and (v) are inhibited in formation of 3-D structures and migration by treatment with chloroquine.

2. The population of DCIS cells of claim 1, wherein said cells express an increased level of one or more of CD44, COX2 or MMP-14, or a decreased level of CD24 or E-Cadherin compared to monolayer anchorage dependent epithelial cells.

3. An isolated population of living human breast ductal carcinoma in situ (DCIS) cells treated in an artificial serum free culture media comprising buffered salts, epidermal growth factor and insulin, wherein the cells (i) are epithelial in origin, (ii) comprise one or more markers of autophagy, (iii) show at least one genetic difference from normal cells, (iv) form 3-D spheroids or duct-like structures or ball aggregates and (v) are inhibited in formation of 3-D structures and migration by treatment with chloroquine, wherein said genetic difference is selected from the group consisting of a loss of copy number of 6p21.1 to 6p12.3, a loss of heterozygosity at SUPT3H gene, a gain of copy number at 5p12 to 5p13.3 or a gain of copy number at 17q22 to 17q25.1.

4. A method of making a strain of human breast ductal carcinoma in situ (DCIS) cells from a patient comprising (A) establishing in a container a serum-free organ culture supplemented with epidermal growth factor and insulin and comprising fragments of breast tissue containing stroma, adipose and ductal elements, among which are ductal carcinoma in situ lesions, and (B) allowing the tissue to attach to the container and allowing the DCIS cells to migrate out of the tissue such that the DCIS cells without enzymatic dissociation or immortalization spontaneously form 3-D spherical and ductal tubular structures that contain cells that show at least one genetic difference from normal cells.

5. A method of assessing whether a potential therapeutic agent is useful for the treatment of human breast ductal carcinoma in situ (DCIS) comprising administering in vitro said potential therapeutic agent to the population of DCIS cells of claim 1, culturing said cells, and determining whether said therapeutic agent inhibits the growth of said cells, proliferation of said cells or tendency of said cells to invade or metastasize.

6. The method of claim 5, wherein said determination step involves evaluating exposed DCIS cells for autophagy.

7. The method of claim 5, wherein said determination step involves histomorphologically evaluating exposed DCIS cells.

8. A method of assessing whether a potential therapeutic agent is useful for the treatment of human breast ductal carcinoma in situ (DCIS), comprising transplanting a population of DCIS cells of claim 1 to a non-human animal model, administering said potential therapeutic agent to said xenotransplant, and determining whether said therapeutic agent inhibits the growth of said cells, proliferation of said cells or tendency of said cells to invade or metastasize.

9. A method of selecting a treatment for a patient with human breast ductal carcinoma in situ (DCIS), comprising
(A) isolating from said patient human breast ductal carcinoma in situ (DCIS) cells as described in claim 4;
(B) administering in vitro a potential therapeutic agent to said DCIS cells;
(C) culturing said cells; and
(D) determining whether said therapeutic agent inhibits the growth of said cells, proliferation of said cells or tendency of said cells to invade or metastasize; and
(E) selecting a treatment based upon said determination.

10. The method of claim 9, further comprising repeating steps (A) to (D) after a selected treatment has been administered to said patient.

11. A method of monitoring the efficacy of a treatment of a patient with human breast ductal carcinoma in situ (DCIS), comprising
(A) isolating from said patient human breast ductal carcinoma in situ (DCIS) cells as described in claim 4;
(B) administering in vitro said potential therapeutic agent to said DCIS cells;
(C) culturing said cells; and
(D) determining whether said therapeutic agent inhibits the growth of said cells, proliferation of said cells or tendency of said cells to invade or metastasize.

12. The method of claim 11, wherein steps (A) to (D) are performed more than once during the course of treatment.

13. A method of treating breast ductal carcinoma in situ (DCIS) in a patient, or preventing or limiting progression of breast DCIS in a patient, comprising identifying in said patient breast DCIS and administering to the patient having breast DCIS an effective amount of an autophagy inhibitor selected from the group consisting of chloroquine, hydroxychloroquine, 3-methyladenine, clomipramine, ethyl pyruvate and glycyrrhizin.

14. The method of claim 13, wherein the autophagy inhibitor is chloroquine.

15. The method of claim 13, further comprising administering to the patient a chemotherapeutic agent.

16. The method of claim 15, wherein the chemotherapeutic agent is a kinase inhibitor.

17. A method for identifying ductal carcinoma in situ (DCIS) malignant precursor cells, comprising (a) assaying for loss of heterozygosity of SUPT3H gene; (b) assaying for ability to form outgrowths in the presence of chloroquine; and (c) identifying cells that display both loss of heterozygosity and inability to form outgrowths in the presence of chloroquine.

18. A method for treating breast ductal carcinoma in situ (DCIS) in a patient, comprising identifying in said patient breast ductal carcinoma in situ (DCIS) and administering to the patient an effective amount of an autophagy inhibitor, wherein said autophagy inhibitor blocks and/or suppresses autophagy.

19. The method of claim 18, wherein said autophagy inhibitor is chloroquine.

* * * * *